(12) United States Patent
Rossiter et al.

(10) Patent No.: US 10,640,466 B2
(45) Date of Patent: May 5, 2020

(54) ANTHRACENE BASED COMPOUNDS AND THEIR USES

(71) Applicant: UNIVERSITY OF HERTFORDSHIRE HIGHER EDUCATION CORPORATION, Hatfield (GB)

(72) Inventors: Sharon Rossiter, Hatfield (GB); Stewart Brian Kirton, Hatfield (GB); Ramatoulie Camara, Hatfield (GB)

(73) Assignee: UNIVERSITY OF HERTFORDSHIRE HIGHER EDUCATION CORPORATION, Hatfield (GB)

( * ) Notice: Subject to any disclaimer, the term of this patent is extended or adjusted under 35 U.S.C. 154(b) by 0 days.

(21) Appl. No.: 15/571,770

(22) PCT Filed: May 9, 2016

(86) PCT No.: PCT/GB2016/051322
§ 371 (c)(1),
(2) Date: Nov. 3, 2017

(87) PCT Pub. No.: WO2016/181120
PCT Pub. Date: Nov. 17, 2016

(65) Prior Publication Data
US 2018/0118685 A1 May 3, 2018

(30) Foreign Application Priority Data
May 8, 2015 (GB) .................................. 1507937.9

(51) Int. Cl.
C07D 209/94 (2006.01)
C07D 403/04 (2006.01)
A61P 35/00 (2006.01)
C07D 231/14 (2006.01)
C07D 249/08 (2006.01)

(52) U.S. Cl.
CPC ............ C07D 209/94 (2013.01); A61P 35/00 (2018.01); C07D 231/14 (2013.01); C07D 249/08 (2013.01); C07D 403/04 (2013.01)

(58) Field of Classification Search
None
See application file for complete search history.

(56) References Cited

U.S. PATENT DOCUMENTS

| 3,123,618 | A | 3/1964 | Schumann |
| 3,377,353 | A | 4/1968 | Bruce |
| 5,409,932 | A | 4/1995 | Schwenner et al. |
| 5,411,960 | A | 5/1995 | Schwenner et al. |
| 7,655,688 | B2 * | 2/2010 | Salvati .................. A61K 31/403 |
| | | | 514/307 |

FOREIGN PATENT DOCUMENTS

| JP | 2006-508330 A | 3/2006 |
| WO | WO-99/31087 | 6/1999 |

OTHER PUBLICATIONS

Silva, A., Mini-Reviews in Medicinal Chemistry, 2005, vol. 5, pp. 893-014.*
Srivastava, N. et al., Ind. J. Chem. 1991, vol. 30B, pp. 1080-1082.*
CAPLUS 1976:179530.*
CAPLUS 2013:73400.*
Surbhi Arya et al: "Synthesis, anti-inflammatory, and cytotoxicity evaluation of 9, 10-dihydroanthracene-9, 10 -[alpha], [beta]-succinimide and bis-succinimide derivatives", Medicinal Chemistry Research, vol. 22, No. 9, Jan. 5, 2013, pp. 4278-4285.
Aust J Chern et al: "A Study of Conformation about the Aryl C—N Bonds in N-Aryl Imides by Dynamic N", Aust. J. Chern. 1976, 29, Feb. 1, 1976 (Feb. 1, 1976), pp. 295-300.
Edwin Weber et al. "Modular Design of Hosts Involving a Rigid Succinimide Framework and N-Bonded Lateral Groups. Crystalline Inclusion Properties and Crystal Structures of Inclusion Compounds with Dioxane, MeOH, and DMF", J. Org. Chem, Jan. 1, 1991 (Jan. 1, 1991), pp. 7281-7288.
Ek Raj Thapaliya et al: "Photoactivatable Anthracenes" , The Journal of Organic Chemistry, vol. 79, No. 9,May 2, 2014 (May 2, 2014), pp. 3973-3981.
Sergio Bova et al: "Anthracene Based Compounds as New L-type Ca 2+ Channel Blockers: Design, Synthesis, and Full Biological Profile", Journal of Medicinal Chemistry, vol. 52, No. 5, Mar. 12, 2009 (Mar. 12, 2009), pp. 1259-1262.
Padi Lla Laura et al: "S100 to receptor for advanced glycation end-products binding assay: Looking for inhibitors", Biochemical and Biophysical Research Commun Icati Ons, vo 1. 446, No. 1, Apr. 12, 2014 (Apr. 12, 2014), pp. 404-409.

(Continued)

Primary Examiner — Heidi Reese
(74) Attorney, Agent, or Firm — Mannava & Kang, P.C.

(57) ABSTRACT
A compound of the general formula (A)

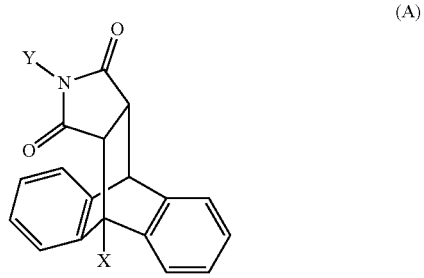

(A)

or a pharmaceutically acceptable salt, solvate, hydrate, polymorph, prodrug, codrug, cocrystal, tautomer, racemate, stereoisomer or mixture thereof, in which: X is independently $NO_2$ or H; and Y is selected from H, amino, amide, ester, carboxy and its esters and amides, alkyl, alkenyl, alkynyl, cycloalkyl, alkaryl, aryl, heterocyclic or heteroaryl groups, all of which can be substituted with heteroatoms and/or side groups, and wherein any chains can be straight or branched is disclosed.

9 Claims, 11 Drawing Sheets

(56) References Cited

OTHER PUBLICATIONS

T. Arumugam et al: "Designing and Developing SIOOP Inhibitor 5-Methyl Cromolyn for Pancreatic Cancer Therapy", Molecular Cancer Therapeutics, vol. 12, No. 5, Jan. 9, 2013 (Jan. 9, 2013), pp. 654-662.
Database Registry [Online] Chemical Abstracts Service, Columbus, Ohio, US; Oct. 3, 2001 (Oct. 3, 2001), 1 page, XP002758222, Database accession No. 3599000-90-6.
Database Pubchem Substance [Online] NCBI; Jul. 12, 2007 (Jul. 12, 2007), 6 pages, XP002758223, Database accession No. SID2117385.
Database Pubchem Substance [Online] NCBI; Dec. 5, 2007 (Dec. 5, 2007), 6 pages, XP002758224, Database accession No. SID43593987.
Database Pubchem Substance [Online] NCBI; May 28, 2009, 6 pages. Database accession No. 59969528.
Database Pubchem Substance [Online] NCBI; Feb. 22, 2011 (Feb. 22, 2011), 6 pages, XP002758226, Database accession No. SID107858392.
Database Pubchem Substance [Online] NCBI; Dec. 5, 2007, 6 pages, Database accession No. SID42149749.
Database Pubchem Substance [Online] NCBI; May 28, 2009 (May 28, 2009), 6 pages, XP002758228, Database accession No. SID59969525.
Database Pubchem Substance [Online] NCBI; May 28, 2009 (May 28, 2009) XP002758229, 6 pages. Database accession No. SID60667449.
Database Pubchem Substance [Online] NCBI; May 30, 2009 (May 30, 2009), 6 pages, XP002758230, Database accession No. SID72361678.
Database Registry [Online] Chemical Abstracts Service, Columbus, Ohio, US; Apr. 24, 2001 (Apr. 24, 2001), 1 page, XP002758231, Database accession No. 332144-99-7.
Database Pubchem Substance [Online] NCBI; Jul. 11, 2005 (Jul. 11, 2005), 6 pages, XP002758232, Database accession No. SID1642982.
Database Pubchem Substance [Online] NCBI; Feb. 22, 2011 (Feb. 22, 2011), 6 pages, XP002758233, Database accession No. SID105218152.
"The International Search Report and the Written Opinion, PCT Application No. PCT/GB2016/051322", International Searching Authority, dated Jun. 15, 2016, 16 pages.
"Combined Search and Examination Report", Application No. GB1510123.1, UK Intellectual Property Office, dated Mar. 4, 2016, 11 pages.
"Combined Search and Examination Report", Application No. GB1608085.5, UK Intellectual Property Office, dated Feb. 13, 2017, 11 pages.
Verma, S. M.; Singh, Rajendra,Conformational studies about the N—N bond by NMR spectroscopy: N—4' —(1', 2', 4' triazolyl) succinimide derivatives, Indian Journal of Chemistry, Section B: Organic Chemistry Including Medicinal Chemistry, Jan. 1978, vol. 16B, pp. 60-63.
Database Registry,2002, RN 433973—17—2, Retrieved from STN international [online]; retrieved on Jan. 14, 2020, 1 page.
Database Registry,2001, RN 359900 to 90 6, pp. 332144 to 99, 7,Retrieved from STN international [online]; retrieved on Jan. 14, 2020, 2 pages.
Japan Patent Office, "Machine English translation of Notice of Reasons for Refusal, JP Application No. 2018-510003", dated Jan. 22, 2020, 3 pages.

* cited by examiner

ANTHRACENE BASED COMPOUNDS AND THEIR USES

CLAIM FOR PRIORITY

The present application is a national stage filing under 35 U.S.C. § 371 of PCT application number PCT/GB2016/051322, having an international filing date of May 9, 2016, which claims priority to British application numbers GB1507937.9, having a filing date of May 8, 2015, and GB1510123.1, having a filing date of Jun. 10, 2015, the disclosures of which are hereby incorporated by reference in their entireties.

FIELD OF THE INVENTION

The present invention relates to compounds and their applicability for use in the treatment or prophylaxis of a disease, in particular for use as in treatment of cancer, in particular for use as in treatment of pancreatic cancer, in particular as inhibitors of S100P/RAGE interaction in pancreatic cancer.

BACKGROUND OF THE INVENTION

Pancreatic cancer ranks as one of the most lethal cancers in the developed world. In North America, it was estimated that of the new 45,220 cases of pancreatic cancer diagnosed in 2013, there will 38,460 deaths in the same year. In the UK, despite the improvements in the survival rates of certain cancers such as breast, bowel, ovarian, and non-Hodgkin's lymphomas, there has been little improvement in the survival rates of pancreatic cancer patients, with less than 3% of people surviving the disease beyond five years. Lack of early clinical markers and the asymptomatic nature of the disease contribute to late diagnosis. Consequently, by the time of diagnosis, surgical intervention at present the only option that will significantly extend life expectancy will usually not be a viable option due to the advanced stage of the disease. Surgery followed by chemotherapy, radiation therapy, or combinations of both, are currently the treatment options available. Such interventions however only offer a modest extension of lifespan, and recurrence is often high highlighting the urgent need for investigations into new targets.

S100P is a calcium-binding protein that is highly expressed in pancreatic cancer in the early stages. It binds to the receptor for advanced glycation end-products (RAGE) extracellularly and promotes cell proliferation, migration, invasion and survival. Its absence in pancreatitis, a condition which pancreatic cancer is sometimes misdiagnosed as, makes it an ideal clinical marker for early detection of the cancer. In addition, the protein has been validated as a druggable target in pancreatic cancer. Cromolyn, an anti-allergy drug has been shown to bind to S100P and inhibit its binding to RAGE in in vitro studies. Cromolyn is however not a viable therapeutic agent due to its low bioavailability—it is quickly excreted from the body after administration. A close analogue, 5-methyl cromolyn, was recently shown to be more efficient in inhibiting S100P/RAGE function than cromolyn—100 nmol/L compared to the latter's 10 µM/L in in vitro studies. A need exists for further therapeutic agents for inhibiting S100P/RAGE function.

SUMMARY OF THE INVENTION

In summary herein are presented a group of compounds for use as in treatment of cancer, in particular as inhibitors of S100P/RAGE interaction in pancreatic cancer.

The compounds have general formula (A):

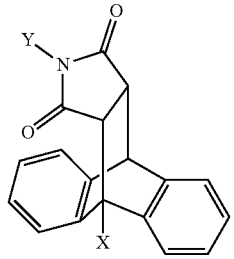

(A)

or may be a pharmaceutically acceptable salt, solvate, hydrate, polymorph, prodrug, codrug, cocrystal, tautomer, racemate, stereoisomer or mixture thereof.

X is independently $NO_2$ or H; and
Y is independently H or a side group.

The compounds all have a lower fused ring system based on nitroanthracene or anthracene. The group Y attached to the N of the succinimide group varies between the compounds. For example, Y may be substituted or non-substituted benzene ring. Alternatively, in some examples Y is a heteroaromatic system. It has been discovered from studies by the inventors that the compounds described below will inhibit S100P/RAGE interaction and are therefore useful for treating pancreatic cancer.

Preferably Y is a hydrogen atom or a suitable substituent group. Example substituent groups include amino, amide, ester, carboxy and its esters and amides, alkyl, alkenyl, alkynyl, cycloalkyl, alkaryl, aryl, heterocyclic or heteroaryl groups, all of which may be optionally substituted with heteroatoms and/or further substituent groups, and wherein any chains of the substituent group or further substituent group may be straight or branched.

Preferably Y is an aromatic or heteroaromatic ring which is substituted or unsubstituted. Substituents are preferably at the 3 or 4 ring position.

Preferably Y has the general formula (B):

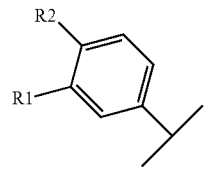

(B)

wherein R1 and R2 are selected from the following combinations:

|       | R1         | R2 |
|-------|------------|----|
| i     | $CO_2H$    | H  |
| ii    | $CO_2Et$   | H  |
| iii   | F          | H  |
| iv    | Cl         | H  |
| v     | F          | H  |
| vi    | $NO_2$     | H  |
| vii   | I          | H  |
| viii  | tBu        | H  |
| ix    | methyl     | H  |
| x     | $OCH_3$    | H  |
| xi    | $N\ CH_3\ CH_3$ | H |

|     | R1    | R2    |
| --- | ----- | ----- |
| xii | CN    | H     |
| xiii | H    | CO$_2$H |
| xiv | H    | CO$_2$Et |
| xv  | H     | F     |
| xvi | H     | Cl    |
| xvii | H    | F     |
| xviii | H   | NO$_2$ |
| xix | H     | I     |
| xx  | H     | tBu   |
| xxi | H     | methyl |
| xxii | H    | OCH$_3$ |
| xxiii | H   | N CH$_3$ CH$_3$ |
| xxiv | H    | CN    |
| xxv | H     | H     |
| xxvi | CO—R3 | H    |
| xxvii | H   | CO—R3 | wherein R3 is selected from:

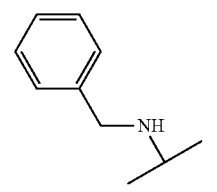

(C)

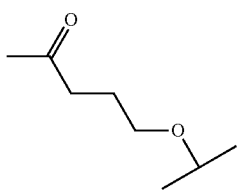

(D)

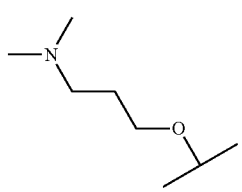

(E)

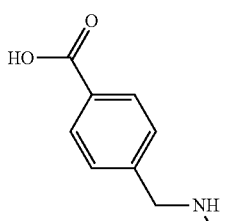

(F)

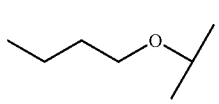

(G)

or alternatively b) wherein Y is an imidazole, a pyrazole, a triazole, or a tetrazole.

Y may be selected from the following the following:

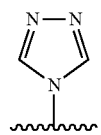

(I)

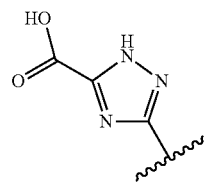

(J)

Where Y has general formula (B), R1 and/or R2 may be esters such as alkyl esters.

Preferably the compound is of general formula (A) wherein Y has general formula (B) and wherein X, R1 and R2 are as follows:

X is NO$_2$, R1 is —CO$_2$H and R2 is H;
X is NO$_2$, R1 is —CO$_2$Et and R2 is H;
X is NO$_2$, R1 is H and R2 is —CO$_2$H;
X is H, R1 is —CO$_2$H and R2 is H;
X is NO$_2$, R1 is H and R2 is H;
X is H, R1 is F and R2 is H;
X is NO$_2$, R1 is Cl and R2 is H;
X is H, R1 is H and R2 is F;
X is H, R1 is H and R2 is Cl; or
X is NO$_2$, R1 is Cl and R2 is H.

Example preferred compounds of general formula (A) according to the invention have X, R1 and R2 has follows when Y has general formula (B):

| X | R1 | R2 |
| --- | --- | --- |
| H | CO$_2$H | H |
| H | CO$_2$Et | H |
| H | F | H |
| H | Cl | H |
| H | F | H |
| H | NO$_2$ | H |
| H | I | H |
| H | tBu | H |
| H | methyl | H |
| H | OCH$_3$ | H |
| H | N CH$_3$ CH$_3$ | H |
| H | CN | H |
| H | H | CO$_2$H |
| H | H | CO$_2$Et |
| H | H | F |
| H | H | Cl |
| H | H | F |
| H | H | NO$_2$ |
| H | H | I |
| H | H | tBu |
| H | H | methyl |
| H | H | OCH$_3$ |
| H | H | N CH$_3$ CH$_3$ |
| H | H | CN |
| H | H | H |
| H | CO—R3 | H |
| NO$_2$ | CO$_2$H | H |
| NO$_2$ | CO$_2$Et | H |
| NO$_2$ | F | H |
| NO$_2$ | Cl | H |
| NO$_2$ | F | H |
| NO$_2$ | NO$_2$ | H |
| NO$_2$ | I | H |

-continued

| X | R1 | R2 |
|---|---|---|
| NO$_2$ | tBu | H |
| NO$_2$ | methyl | H |
| NO$_2$ | OCH$_3$ | H |
| NO$_2$ | N CH$_3$ CH$_3$ | H |
| NO$_2$ | CN | H |
| NO$_2$ | H | CO$_2$H |
| NO$_2$ | H | CO$_2$Et |
| NO$_2$ | H | F |
| NO$_2$ | H | Cl |
| NO$_2$ | H | F |
| NO$_2$ | H | NO$_2$ |
| NO$_2$ | H | I |
| NO$_2$ | H | tBu |
| NO$_2$ | H | methyl |
| NO$_2$ | H | OCH$_3$ |
| NO$_2$ | H | N CH$_3$ CH$_3$ |
| NO$_2$ | H | CN |
| NO$_2$ | H | H |
| NO$_2$ | CO—R3 | H |

Preferably the compound is a substituted 3,4-(9',10'-dihydroanthracene-9',10'-diyl) succinimide, more preferably N-substituted and even more preferably 9'-nitro substituted.

According to a further aspect of the invention there is provided a pharmaceutical composition comprising one or more compounds as described above and pharmaceutically acceptable excipients, adjuvants, diluents and/or carriers.

The pharmaceutical composition may comprise at least one further active agent.

Suitable disintegrators include but are not limited to; agar-agar, algins, calcium carbonate, cellulose, colloid silicon dioxide, gums, magnesium aluminium silicate, methylcellulose, and starch.

Suitable binders include but are not limited to hydroxymethyl cellulose, hydroxypropylcellulose, microcrystalline cellulose, and polyvinylpyrrolidone.

Suitable fillers include but are not limited to calcium carbonate, calcium phosphate, tribasic calcium sulphate, calcium carboxymethylcellulose, cellulose, dextrin, dextrose, fructose, lactitol, lactose, magnesium carbonate, magnesium oxide, maltitol, maltodextrins, maltose, sorbitol, starch, sucrose, sugar, and xylitol.

Suitable lubricants include but are not limited to agar, ethyl laureate, ethyl oleate, glycerin, glyceryl palmitostearate, glycols, hydrogenated vegetable oil, magnesium oxide, mannitol, poloxamer, sodium benzoate, sodium lauryl sulphate, sodium stearyl, sorbitol, stearates, and talc.

Suitable adjuvants include but are not limited to buffer substances, colorants, consistency-improving agents, diluents, emollients, flavour-improving agents, preservatives, salts for varying the osmotic pressure, solubilisers, stabilisers, wetting and emulsifying agents, masking agents and antioxidants.

Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting-point wax, cocoa butter, water, alcohols, polyols, glycerol, vegetable oils and the like.

The pharmaceutical composition may also comprise at least one further active agent, which may include one or more further organic or inorganic molecule.

The composition may be used alone, without further medication. Alternatively, the composition may be used in combination with other medicaments, such as medicaments for treating cancer, in particular pancreatic cancer.

According to a further aspect of the invention there is provided a compound as described above for use as a medicament. In a further alternative the medicament is for use in the treatment or prophylaxis of a disease.

According a further aspect of the invention there is provided a compound as described for use in a method of treatment or prophylaxis of a disease.

According to a further aspect of the invention there is provided a compound as described above for manufacturing a medicament intended for the treatment or prophylaxis of a disease.

According to a further aspect of the invention there is provided a pharmaceutical composition comprising a compound as described above and pharmaceutically acceptable excipients, adjuvants, diluents and/or carriers for use in the treatment or prophylaxis of a disease.

According to a further aspect of the invention there is provided a pharmaceutical composition comprising a compound as described above and pharmaceutically acceptable excipients, adjuvants, diluents and/or carriers for use in a method of treatment or prophylaxis of a disease.

According to a further aspect of the invention there is provided a method of treatment of a disease or condition of the human or animal body comprising administering a therapeutically effective amount of a compound as described above or a pharmaceutical composition as described above.

According to a further aspect of the invention there is provided a compound as described above for use in treating cancer.

According to a further aspect of the invention there is provided a compound as described above for use in treating pancreatic cancer.

According to a further aspect of the invention there is provided a compound as described above wherein the compound inhibits an interaction between S100P and a receptor for advanced glycation end-products.

According to a further aspect of the invention there is provided a compound as described above wherein the compound inhibits S100P/RAGE interaction.

According to a further aspect of the invention there is provided a method of treating cancer comprising the step of administering to a mammal a therapeutically effective amount of a compound as described above. In particular the cancer may be pancreatic cancer. In particular the mammal may be a human.

The term substituted as used herein includes a group in which one or more of the hydrogen atoms have been substituted by another group.

In all aspects of the present invention previously discussed, the invention includes, where appropriate all enantiomers, diastereoisomers and tautomers of the compounds of the invention. If compounds of the invention may exist as stereoisomers and/or geometric isomers—e.g. they may possess one or more asymmetric and/or geometric centres and so may exist in two or more stereoisomeric and/or geometric forms, the present invention contemplates the use of all the individual stereoisomers and geometric isomers of those compounds and mixtures thereof.

BRIEF DESCRIPTION OF THE DRAWINGS

Other aspects and features of the present invention will become apparent to those ordinarily skilled in the art upon review of the following description of specific embodiments of the invention in conjunction with the accompanying figures.

FIG. 1 illustrates S100P interaction with cromolyn.

FIG. 3 illustrates the anti-proliferative effect of cromolyn on pancreatic cancer cells.

DETAILED DESCRIPTION OF PREFERRED EMBODIMENTS

In Silico, Synthetic and In Vitro Studies of Potential Inhibitors of S100P/RAGE Interaction in Pancreatic Cancer More than 95% of people diagnosed with pancreatic cancer will not survive for more than 5 years and, as yet, there is no effective drug treatment. Here we describe the design, synthesis and evaluation of novel small molecules with the potential to bind to, and inhibit S100P, a small calcium-ion binding protein that has been proposed as a drug target against the cancer. We report on one particular compound that has shown >90% potency against pancreatic cancer cell proliferation in in vitro studies comparable to cromolyn, the allergy drug that has been shown to bind to S100P.

Two experimental structures of S100P exist in the RCSB Protein Data Bank (PDB) as an x-ray crystal structure (PDB Accession Code 1J55) and an NMR ensemble (PDB Accession code 1OZO). The former is resolved as a 2 Å monomer with bound calcium ions but with residues 46-51 and 95 missing. The NMR ensemble on the other hand contains conformers that exist as dimers but with no bound calcium ions. There are also three mutations in the ensemble compared to the crystal structure; T6→A, C85→S, and A92→T.

Using the available experimental information on cromolyn binding and the experimental S100P structures, this study employed in silico methods to identify potential binding pockets in the NMR ensemble of S100P to which cromolyn could bind. Subsequent virtual screening of lead-like databases identified hits—structurally distinct from cromolyn—that show promise as chemotherapeutic agents that work against the invasion and growth of pancreatic cancer. Here, we report our findings on the potency of one of the main hits identified—and four analogues—against BxPC-3 and Panc-1 pancreatic cancer cells. The former express endogenous S100P while the latter lack it.

In Silico Design

Conformer number 15 in the NMR ensemble of S100P (1OZO) was identified as the most suitable structure for beginning drug discovery studies after four different pocket detecting algorithms—Fpocket, Pocket-Finder, Q-Site-Finder and Site-Finder—independently identified a pocket at the S100P dimeric interface that was large enough to bind cromolyn. This model coincidentally happens to be most representative model of 1OZO according to the authors who resolved the NMR ensemble.

Figure 1A:
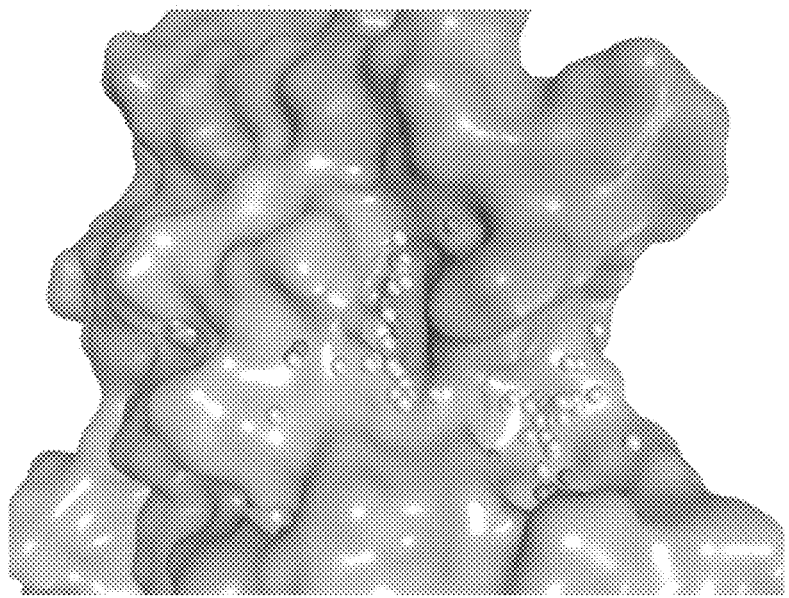
FIG. 1A illustrates two overlapping pockets identified at the dimeric interface of the protein rendered with dummy atoms in MOE.
Figure 1B:
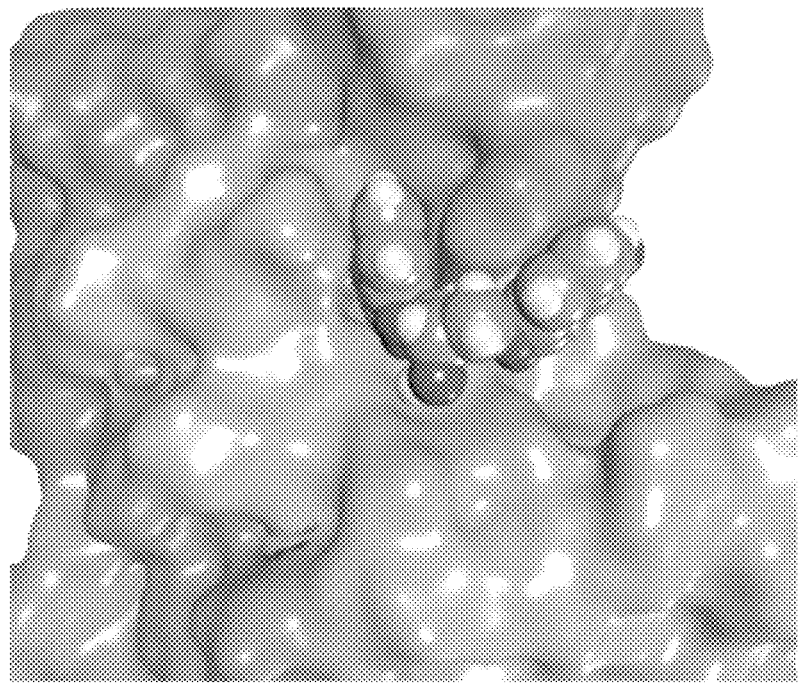
FIG. 1B illustrates cromolyn (space-filling model) docked into pockets.

The residues making up the pocket were located on both chains of the homodimer. Limitations of the pocket detection algorithms result in the pocket at the dimeric interface being resolved as two separate binding sites. The larger of the two pockets has a volume of 349 Å3 (Q-SiteFinder) with residues M1, T2, E5, T6, M8, G9, I12, F71, S72, and I75 from chain A, and F44, V78, A79, A80, I81, T82, S83, A84, C85, H86, K87, Y88, F89, K91, A92, G93, L94, and K95 from chain B contributing to the pocket surface. The smaller pocket is more buried than the first and has a volume of 198 Å3 with residues G9, I11, I12, D13, F15, S16, S19, S21, Q26, F71, S72, F74, I75, and V78 from chain A, and T82 and H86 from chain B contributing to the pocket surface (FIG. 1). F15, Y88 and F89 are involved in the hydrophobic core of S100P which, is exposed when the protein undergoes a conformational change upon calcium-ion binding. The same pockets identified by the other programs were found to be sub-sets of those identified by Q-SiteFinder. In Site-Finder where identified cavities are ranked according to their propensity for ligand binding (PLB) score, the pockets identified at the dimeric interface were ranked in the top three with respect to propensity for ligand binding. In contrast to recently published work on S100P-cromolyn interaction where it was reported that identified pockets on the protein were symmetrical, such was not observed in our study. Indeed, none of the pockets identified on the structures in the NMR ensemble show symmetricity. However, residues E5, D13, F44, Y88 and F89 of S100P that were identified by the same group in a functional assay to play a vital role in RAGE binding were also identified in our pockets.

Figure 1C:
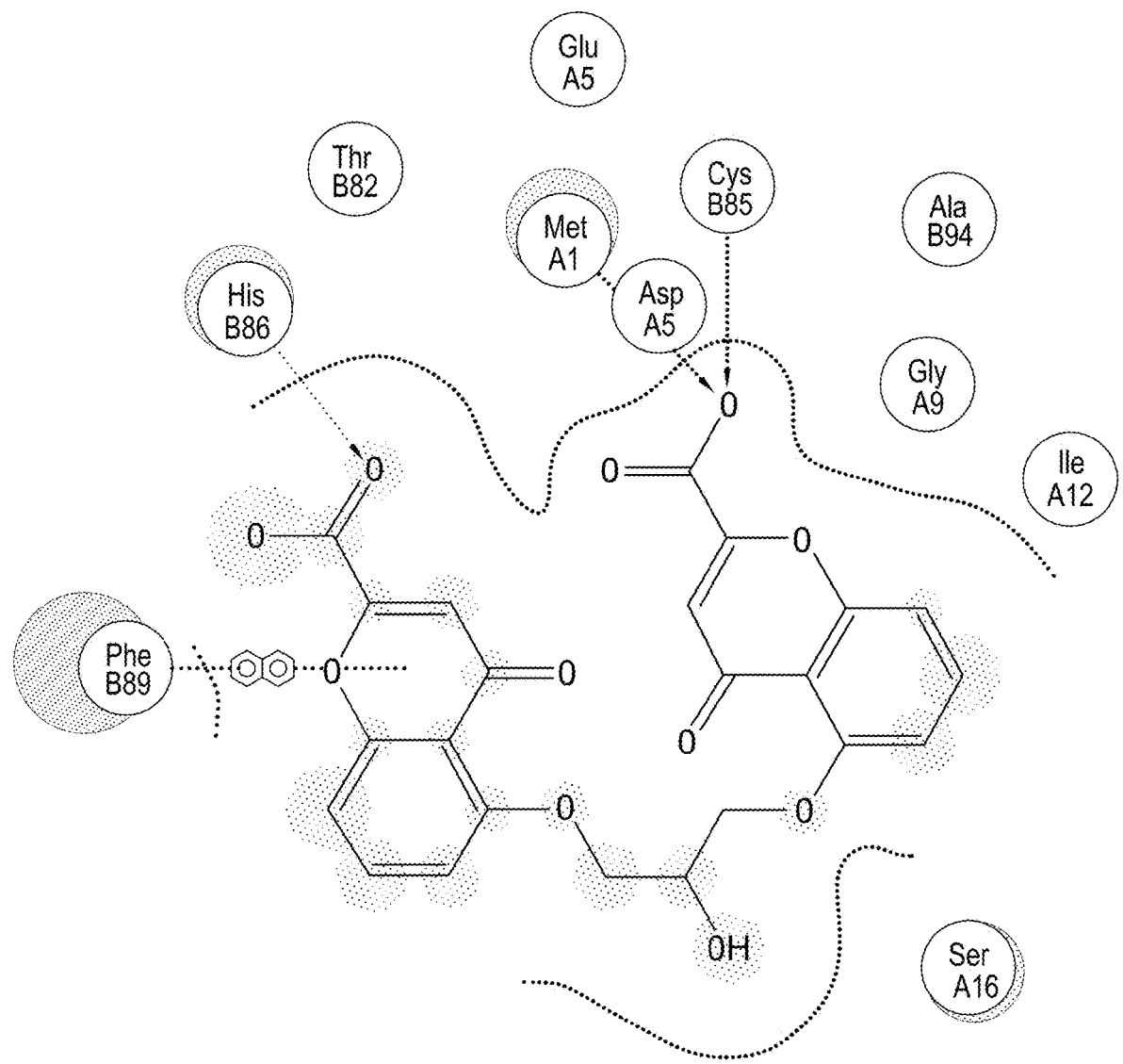
FIG. 1C illustrates predicted binding interactions between cromolyn and S100P.

When cromolyn was docked into these pockets (FIG. 1B) using the Dock tool in MOE, the pose with the most interactions with the protein—three in total—had an estimated binding affinity score (S) of −10.54 kcal/mol. This pose had two hydrogen bond-interactions between the carboxylate oxygen at one end of the ligand and residue H86, and between the carboxylate oxygen at the other end with residue C85. The third interaction involved a pi-stacking hydrophobic interaction between residue F89 and one of the benzoxazine moieties of the ligand (FIG. 1C). These interactions served as the basis for a three-point pharmacophore model that was used to virtually screen lead-like databases in the MOE library. Combined, these databases had 653,214 compounds and the virtual screen returned 4,610 hits-0.7% of the databases. ChemAxon's Library MCS clustering tool (JChem 5.9.0, 2013) available from ChemAxon (http://www.chemaxon.com) was used to cluster the hits based on their chemical similarity. There were 129 clusters with 24 singletons. The hit with the lowest binding affinity energy score (S) was selected from each cluster to give a diverse collection of hits with low binding affinity scores. Due to limited resources and availability of compounds from commercial vendors, 12 compounds were purchased from Chembridge Corporation (San Diego, USA) and InterBioscreen (Moscow, Russia) and five were synthesised in-house. These were subjected to biological screenings against pancreatic cancer cells.

Biological Screening

Compound 2 was one of seventeen compounds from the virtual screen that were subjected to a Matrigel invasion assay (Corning®, USA) screening against BxPC-3 and Panc-1 pancreatic cancer cells. BxPC-3 cells express endogenous S100P while Panc-1 cells do not. Initially purchased from ChemBridge, this compound—and analogues—were further synthesised and purified in the lab after invasion assay screening against BxPC-3 showed a promising effect on these cells (FIG. 2).

Figure 2A:
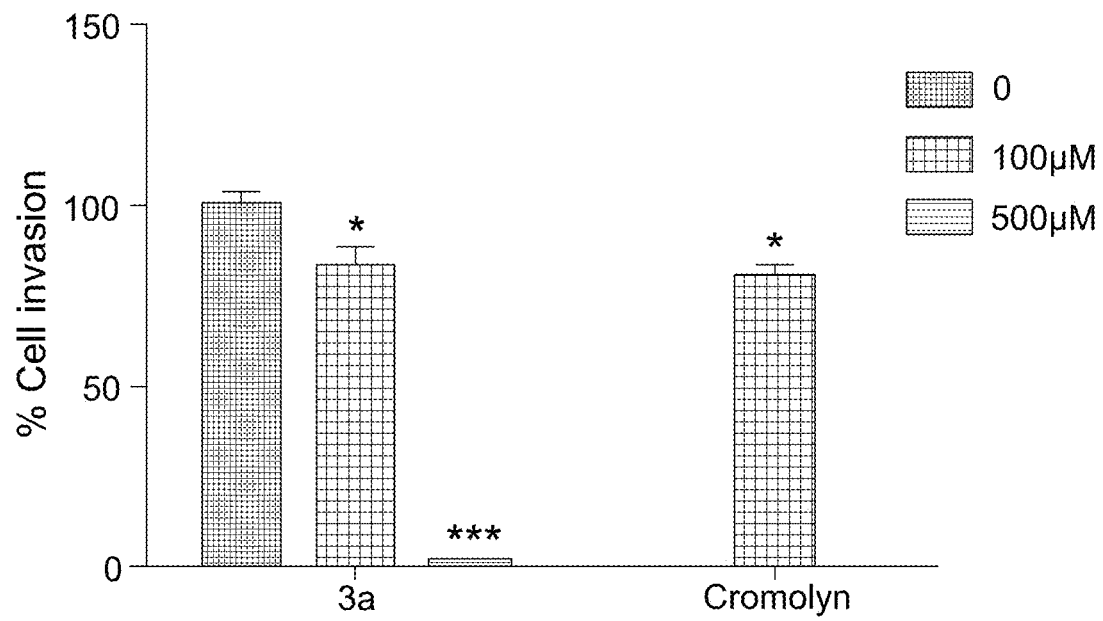
FIG. 2A illustrates the results when compound 2 was added to serum-free medium in the upper compartment of Matrigel invasion chamber along with the BxPC-3 cells; while media with 10% serum was added to lower chamber. After 48 hours, cells that had invaded onto the lower surface of the membrane were stained using Giemsa stain and cells in 5 different fields were counted for invasion studies. Results are expressed as the mean±SEM. P value of <0.05 (*), <0.01 () and <0.001 (*) was determined relative to control using 2-Way ANOVA. Photographs of representative membranes for cells after Giemsa staining when the cells were exposed in FIGS. 2B, 2C, 2D and 2E.
Figures 2B, 2C, 2D, 2E:
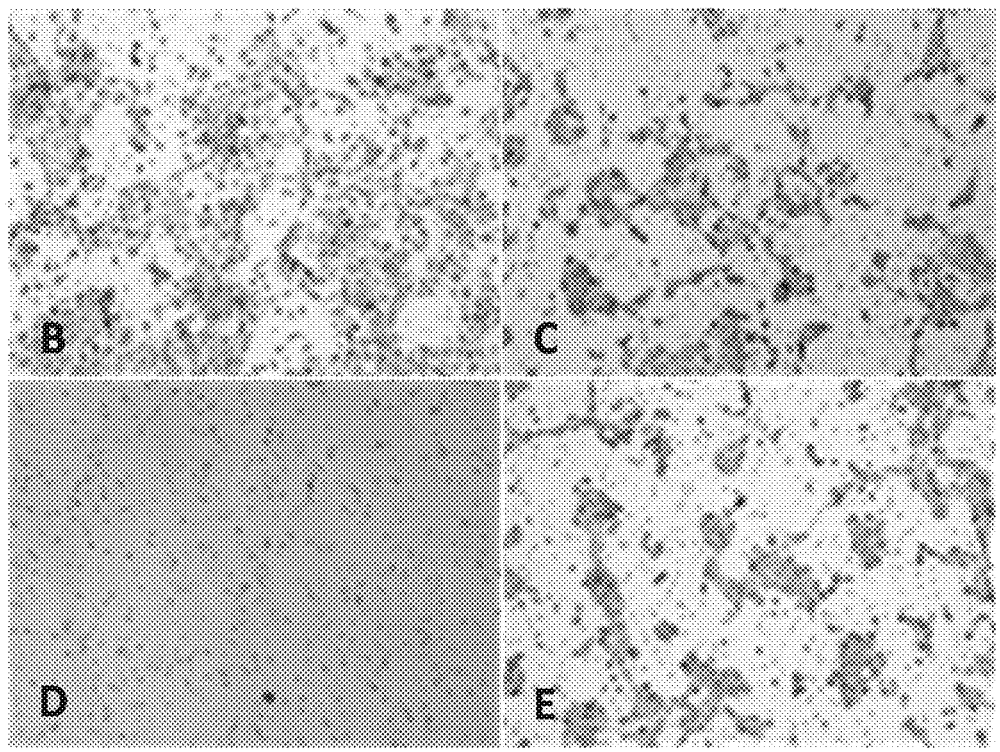
FIG. 2 illustrates the effect of 2 and cromolyn (100 μM) BxPC-3 invasion.
Figure 3A:
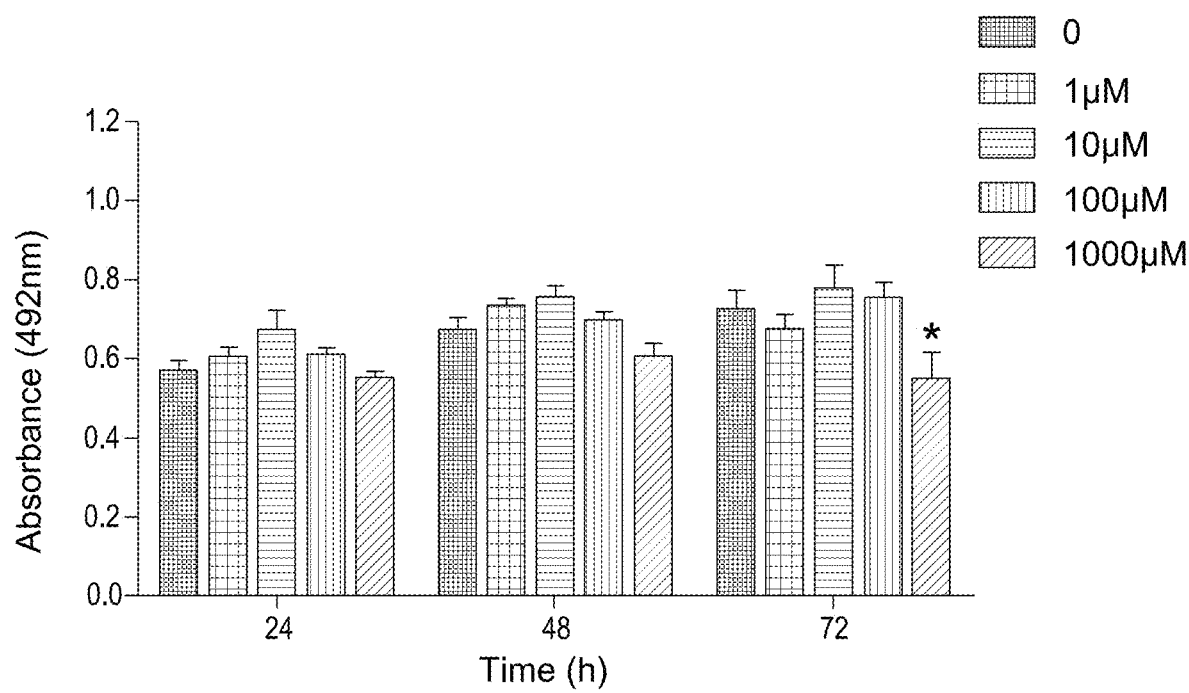
FIG. 3A illustrates BxPC-3.
Figure 3B:
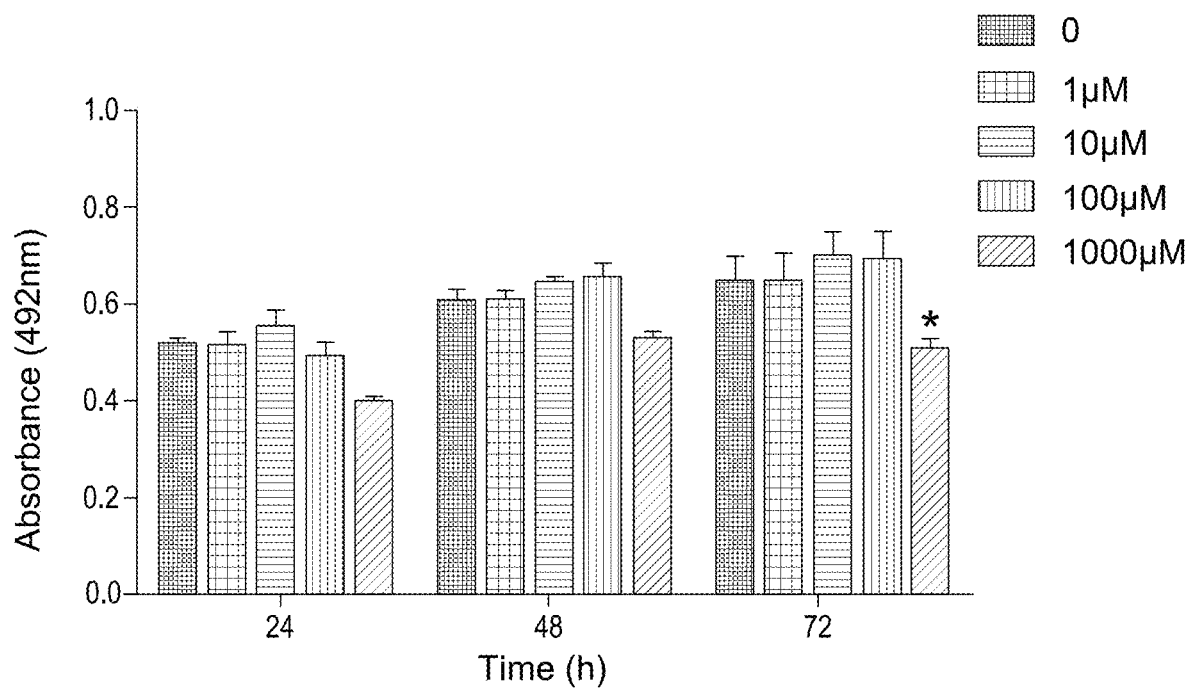
FIG. 3B illustrates Panc-1 cells. Cells were seeded overnight (104 cells/well) in 96 well plates in complete medium supplemented with 10% v/v FBS, 2 mM L-glutamine and 200 U Penicillin/Streptomycin solution. Compounds were serially diluted into the wells and cell proliferation assessed using MTS assay after 24, 48, and 72 hours. Results are expressed as mean±SEM with n=4. P value of <0.05 (*), <0.01 (), <0.001 (*) and <0.0001 (****) was determined relative to control using 2-Way ANOVA. Post-test comparisons were made using Bonferroni test at 95% confidence interval.

At 100 and 500 µM, there was a 17% ($p<0.05$) and 100% ($p<0.001$) reduction in invasion of BxPC-3 cells respectively across the Matrigel matrix (FIG. 2). No effect was seen on Panc-1 cells (data not shown). In comparison, cromolyn at 100 µM inhibited invasion of these cells by 20% ($p<0.05$, FIG. 2). Cromolyn was shown in previous studies to reduce the proliferation and invasion of pancreatic cancer tumours in mice models. However, inhibition of growth and invasion of these cells was more noticeable in combination with Gemcitabine, an anti-cancer drug currently used to treat pancreatic cancer, compared to when cromolyn is administered on its own. A similar study of cromolyn on Panc-1 cells by the same authors showed no significant effect on invasion and proliferation, implying an S100P-specific effect from cromolyn on BxPC-3 cells. In this study, no significant effect was observed against the proliferation of both BxPC-3 and Panc-1 cells (FIG. 3) except at the higher concentration of 1000 µM.

Figure 4A:
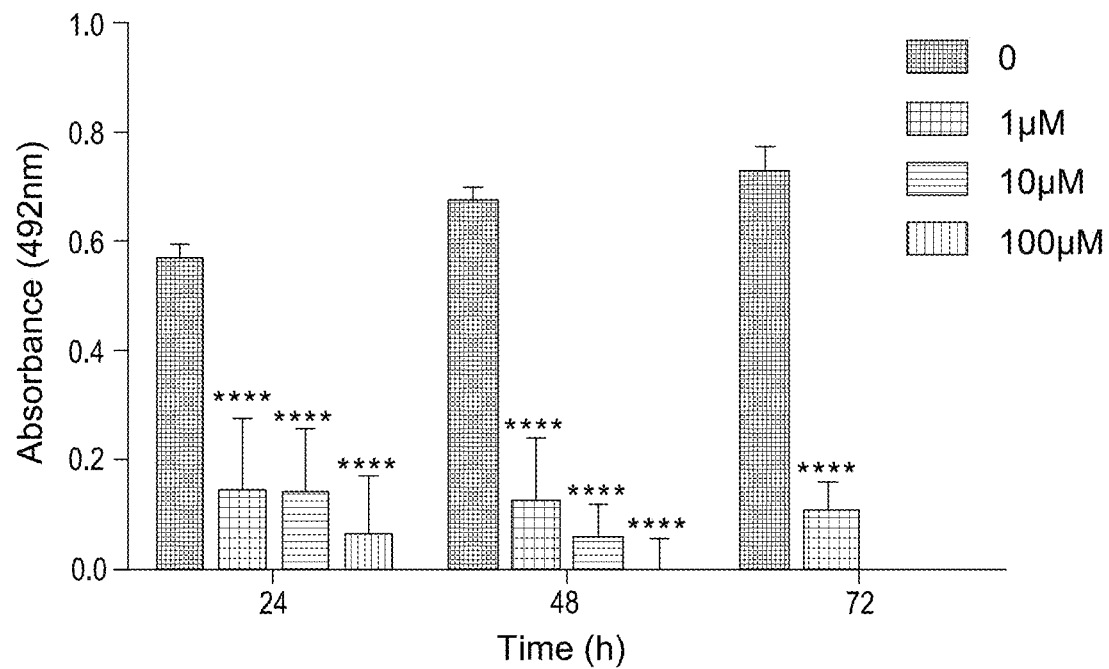
FIG. 4 illustrates the anti-proliferative effects of compounds 2 (A), 3 (B), 8 (C), 26 (D) and 7 (E) on BxPC-3 cells. BxPC-3 cells were seeded overnight ($10^4$ cells/well) in 96-well plates in complete RPMI-1640 medium supplemented with 10% v/v FBS, 2 mM L-glutamine and 200 U Penicillin/Streptomycin solution. Compounds were serially diluted into the wells and cell proliferation assessed using MTS assay after 24, 48, and 72 hours. Results are expressed as mean±SEM with n=4. P value of <0.05 (*), <0.01 (), <0.001 (*) and <0.0001 (****) was determined relative to control using 2-Way ANOVA. Post-test comparisons were made using Bonferroni test at 95% confidence interval.
Figure 4B:
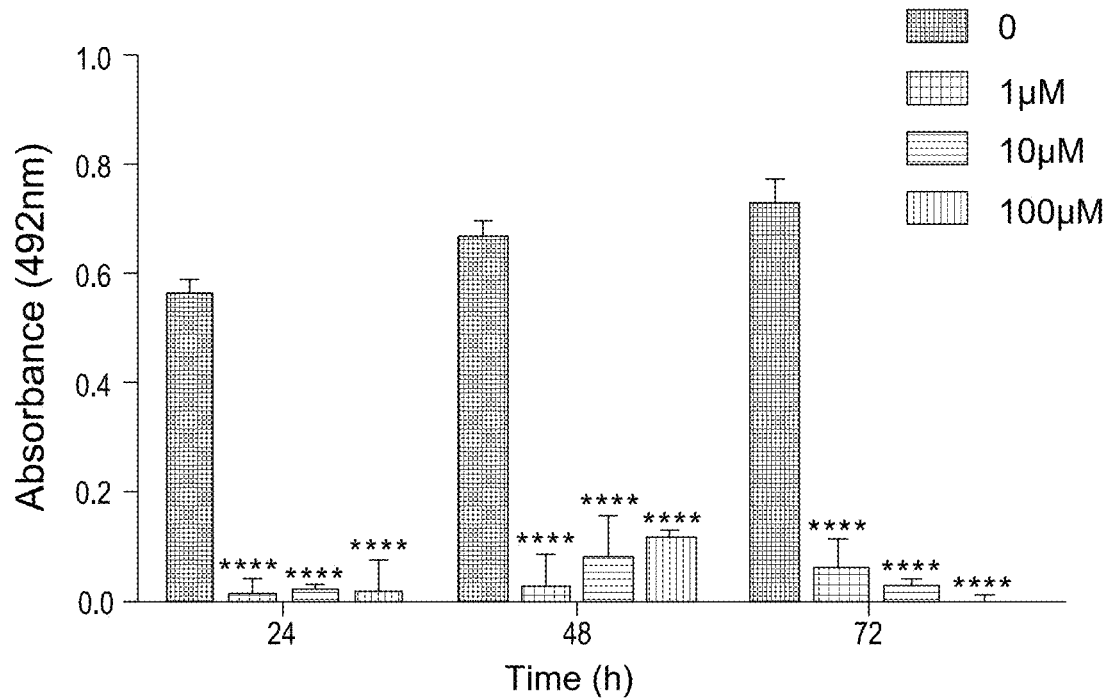

When compound 2 was screened for anti-proliferation properties on BxPC-3 and Panc-1 cells, there was a noticeable inhibition of growth of BxPC-3 relative to control ($p<0.001$, FIG. 4A) for all three concentrations after 72 h. However, a similar effect was also observed on the Panc-1 cells, casting doubt upon a solely S100P-mediated effect (see Supplementary Information). Compound 3, with the ester group in place of the acid, had a more pronounced anti-proliferative effect on BxPC-3 after 24 h compared to 2 (FIG. 4B). This initial decrease in metabolic activity may be due to exposure of the cells to a foreign stimulus resulting in a lower proliferative ability. After 48 h, the cells appear to be recovering albeit only slightly compared to the control.

Figure 4C:
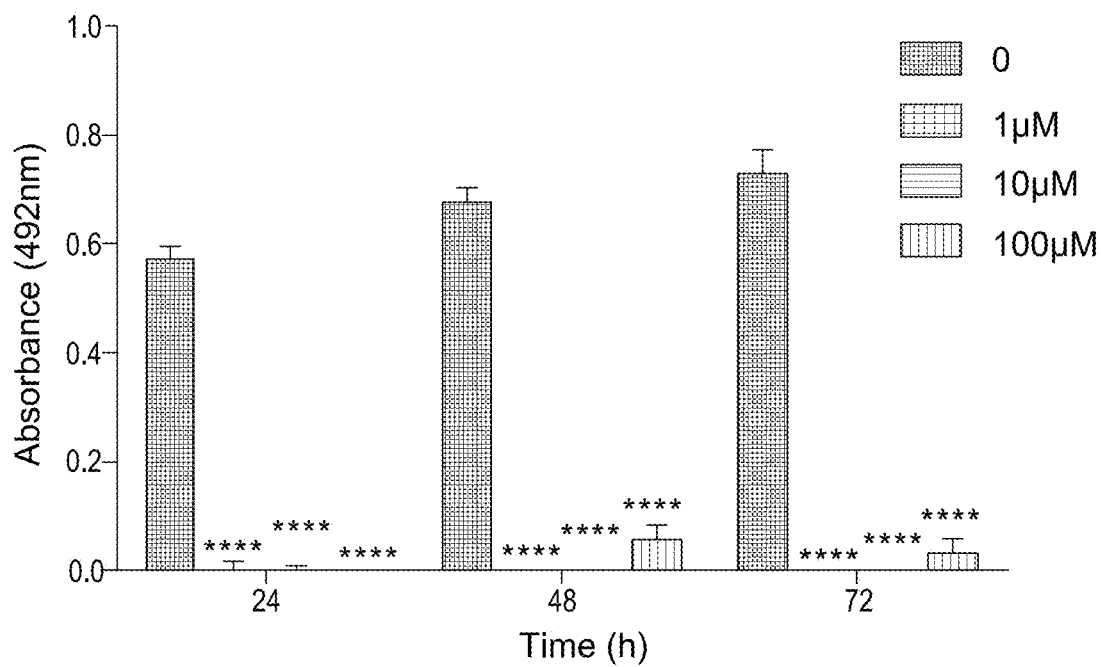
Figure 4D:
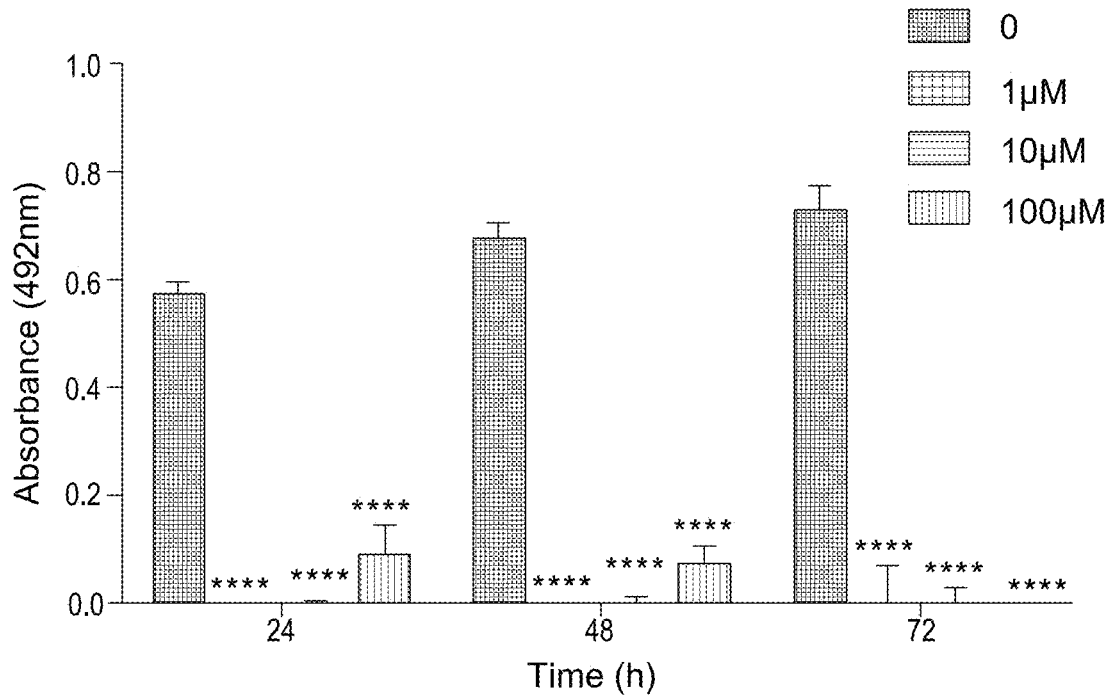
Figure 4E:
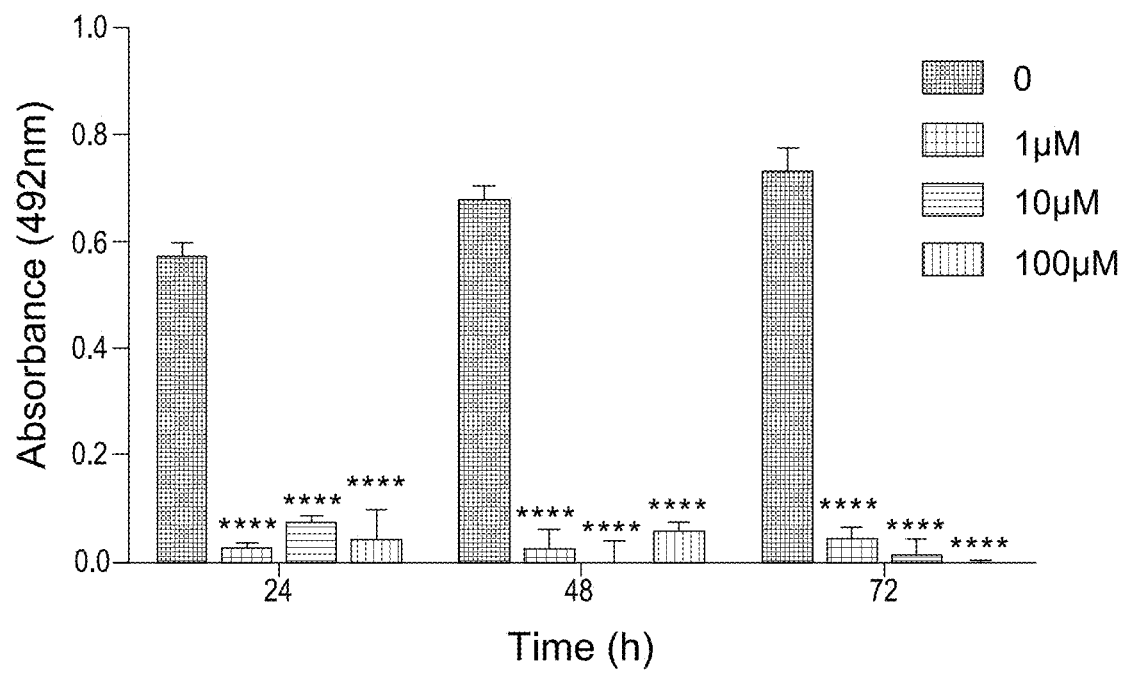
Figure 5A:
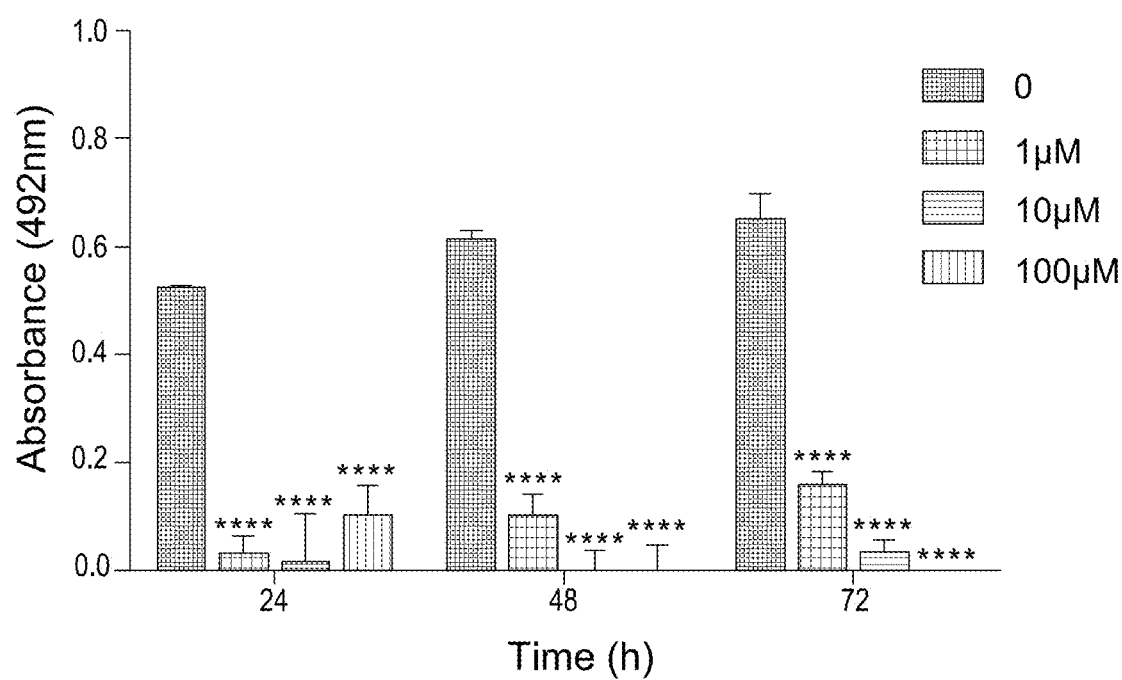
FIG. 5 illustrates anti-proliferative effect of compounds 2 (A), 3 (B), 8 (C), 26 (D) and 7 (E) on Panc-1 cells. Panc-1 cells were seeded overnight ($10^4$ cells/well) in 96-well plates in complete DMEM medium supplemented with 10% v/v FBS, 1% v/v L-glutamine and 200 U Penicillin/Streptomycin solution. Compounds were serially diluted into the wells and cell proliferation analysed using MTS assay after 24, 48, and 72 hours. Results are expressed as mean±SEM with n=4. P value of <0.05 (*), <0.01 (), <0.001 (*) and <0.0001 (****) was determined relative to control using 2-Way ANOVA. Post-test comparisons were made Bonferroni test at 95% confidence interval.
Figure 5B:
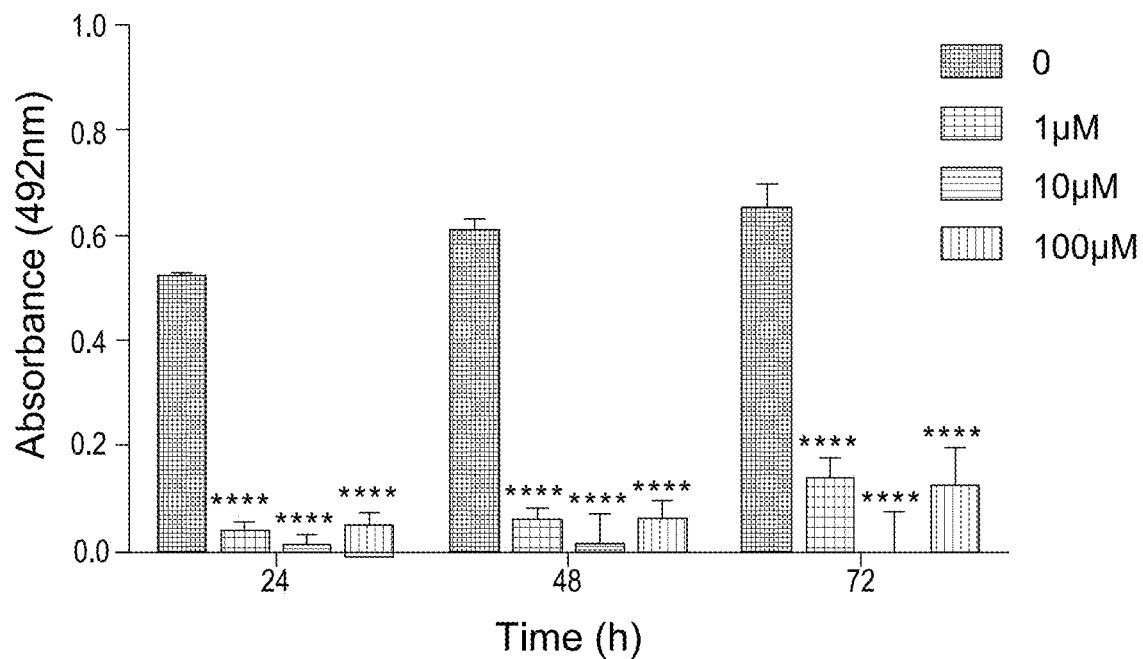
Figure 5C:
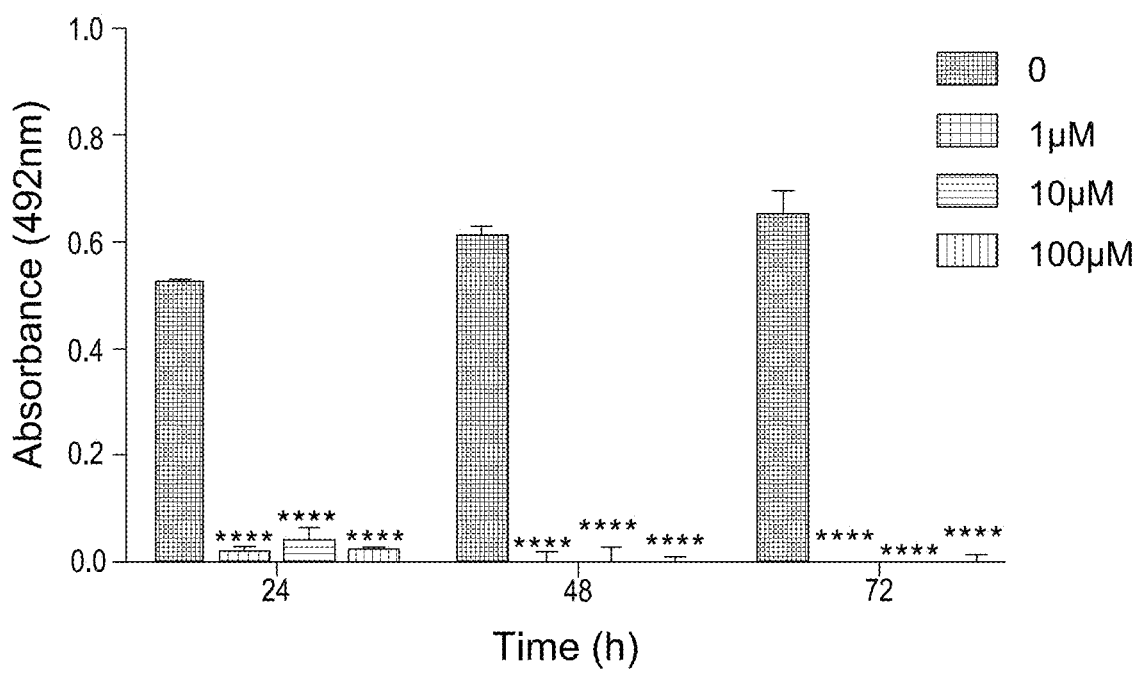
Figure 5D:
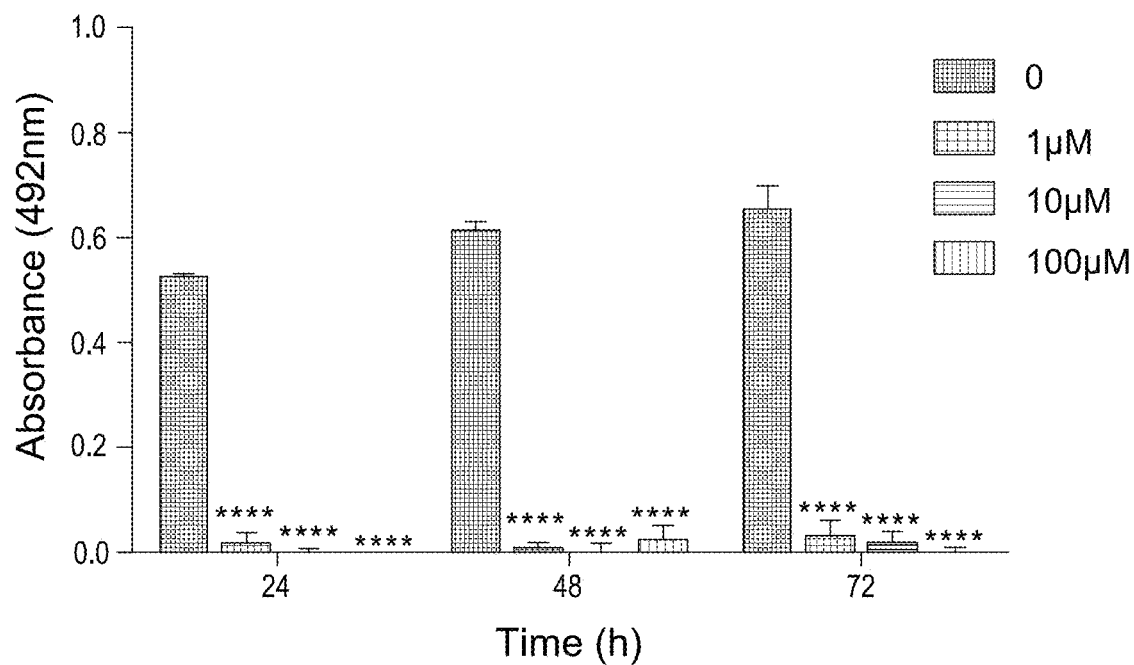
Figure 5E:
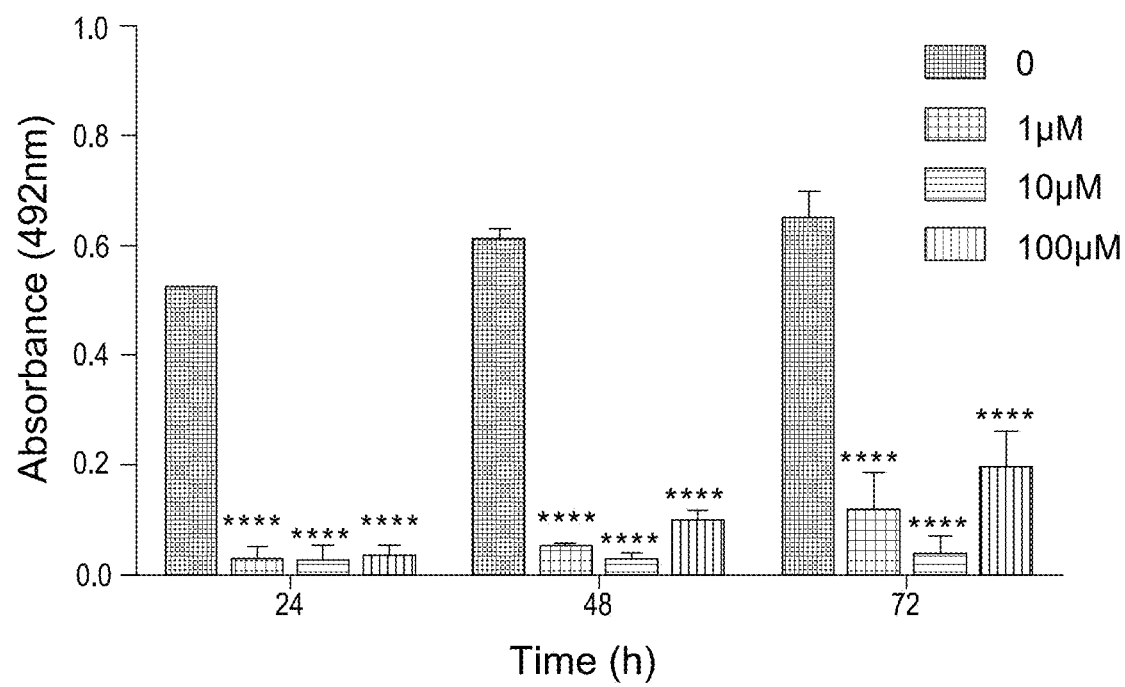

When the acid group is in the ortho-position—compound 8—the anti-proliferative effect on BxPC-3 is more pronounced at 1 and 10 µM compared to 2 where the acid group is in the meta-position (FIG. 4C). Although still viable as assessed by trypan blue counting, no metabolic activity was observed for the BxPC-3 cells at 1 µM which opens up a promising avenue for further studies at sub-micromolar concentrations. What is even more encouraging is that initial results from an S100P/RAGE functional assay screening currently underway indicate nanomolar inhibition from this compound against S100P binding to RAGE, therefore confirming that the compound is acting on S100P, although selectivity has yet to be achieved. Compounds 26 and 7, which lacked the $NO_2$ group and the acid group respectively, both inhibited proliferation of BxPC-3 cells at low concentrations (1 and 10 µM) relative to control (FIGS. 4D and 4F respectively). Again, inhibition was unfortunately observed against Panc-1 cells. At 100 µM and above, solubility issues were observed with compounds 3, 8 and 7: these compounds were precipitating in the culture media and interfering directly with the assay resulting in an erroneous high absorbance reading. However, since inhibition of proliferation was observed at concentrations of <10 µM, with no obvious solubility issues, the feasibility of formulating these novel compounds into potential anti-cancer therapeutics remain a true possibility.

Cell Lines

All reagents for in vitro studies were purchased from Sigma Aldrich (Dorset, UK) unless otherwise specified. Human pancreatic cancer cells, Panc-1 (ATCC® CRL-1469™) and BxPC-3 (ATCC® CRL-1687™), were purchased from LGC Standards (LGC Ltd., Middlesex, UK). Both were cultured in their respective culture medium—Dulbecco Modified Eagle Medium (DMEM) for Panc-1 and RPMI-1640 for BxPC-3 supplemented with 10% v/v Foetal Bovine Serum (FBS), 200U Penicillin/Streptomycin solution, and 2 mM L-glutamine. Both cells were maintained at 37° C. in a 5% humidified $CO_2$ atmosphere and passaged at least three times a week when they have reached about 70% confluency using a standardised trypsinisation protocol. Cromolyn was purchased as a sodium salt while compounds 2, 3, 7, 8 and 26 were synthesised, characterised and purified at the University of Hertfordshire. To prepare stock concentrations (10 mM), cromolyn was dissolved in distilled water while compounds 2, 3, 7, 8 and 26 were dissolved in DMSO.

Matrigel Invasion Assay

Matrigel invasion assay were carried out using transwell inserts with 8-µm pore size (BD-Bioscience, Oxford, UK) and Biocoat Matrigel Invasion plates (BD-Bioscience, Oxford, UK). Plates were removed from storage at −20° C. and kept at room temperature (~19° C.) for two hours prior to using to equilibrate the gel. Pre-warmed serum-free medium (500 µL) was added to the upper chamber of the inserts and incubated for a further two hours at 37° C. in a humidified $CO_2$ atmosphere. The medium was removed and 200 µL of cell suspension ($2.5\times10^4$ cells/mL) in serum-free culture media were pipetted into each insert. The inserts were gently transferred into the wells which contained 500 µL of culture medium supplemented with 10% FBS. The plates were incubated in a humidified $CO_2$ incubator at 37° C. for 48 h. The top solution was then removed and cells on the upper surface of the membrane were gently removed with sterile cotton-tip swabs. Cells on the bottom surface of the inserts were fixed in 100% methanol and stained with 0.4% (w/v) Giemsa stain (Sigma Aldrich, Poole, UK). The chambers were sequentially washed with distilled water and then air dried. The number of cells from five adjacent fields of view from each of the membranes were counted at a ×10 magnification to obtain the average number of cells per field. Data are expressed as the percent invasion through the Matrigel matrix and membrane relative to the invasion through the control membrane.

CellTiter 96® AQueous One Solution Cell Proliferation Assay (MTS) Studies

Pancreatic cancer cells ($1\times10^5$ cells/mL) in 100 µL complete cell culture medium were plated in 96-well plates (Sigma-Aldrich, Poole, UK) and incubated overnight at 37°

C., 5% $CO_2$ atmosphere. Cromolyn and compounds 2, 3, 7, 8 and 26 were prepared from stocks of 10 mM in serum-free medium and serially diluted to give 1, 10, 100 and 1000 μM. Control samples for this study included cells without any drugs, cell samples with DMSO at the corresponding concentration(s) and media-only samples. Cells were incubated with test compounds for 24, 48 and 72 h. At each time point i.e. 24, 48 and 72 h, CellTiter 960 AQueous Non-Radioactive Cell Proliferation Assay (MTS) (Promega, UK) was added to each well (1:5). Plates were incubated for 90 minutes before reading the absorbance at 492 nm using a Multiskan Ascent 96/384 plate reader (Thermo Scientific, Loughborough, UK). The experiments were repeated three times.

For data analysis, background noise (media only wells) was subtracted from all wells. DMSO absorbance at 1, 10, 100 and 1000 μM was subtracted from wells with sample compounds before an average of all four replicates was taken. Data is plotted as mean from three repeats ±SEM with p value set at 0.05.

Synthesis

Reagents for the chemical synthesis unless specified were purchased from Sigma-Aldrich (Gillingham, Dorset, UK) and were used without further purification. All solvents were purchased from Fisher Scientific (Loughborough, UK). Where necessary, solvents were dried using 3 Å (e.g. methanol) and 4 Å (e.g. diethyl ether) molecular sieves. $^1$H-NMR and $^{13}$C-NMR (TMS as standard) spectra were recorded on a Jeol ECA600/54/SSS spectrometer. Chemical shifts are given in ppm relative to tetramethylsaline and J values (where given) are in Hz. Infrared spectra were recorded on a Nicolet 6700 FT-IR Smart iTR (Thermo Scientific) spectrometer using a Perkin Elmer FT-IR/FIR Spectrometer Frontier, with samples prepared as thin films on the universal ATR sampling accessory. LC-MS was measured on a Varian system with 2×210 LC pumps, a 400 autosampler and a 1200 L mass spectrometer. Melting points were measured using a Griffin melting point apparatus and are uncorrected. Thin-layer chromatography (TLC) was conducted on silica gel plates pre-coated with fluorescent indicator $UV_{254}$ (TLC-sheets POLYGRAM® SIL G/$UV_{254}$, Fisher, UK). IUPAC names for compounds were generated using ChemBioOffice Ultra 14.

9-Nitro-9,10-dihydro-9,10-[3,4]furanoanthracene-12,14-dione (1)

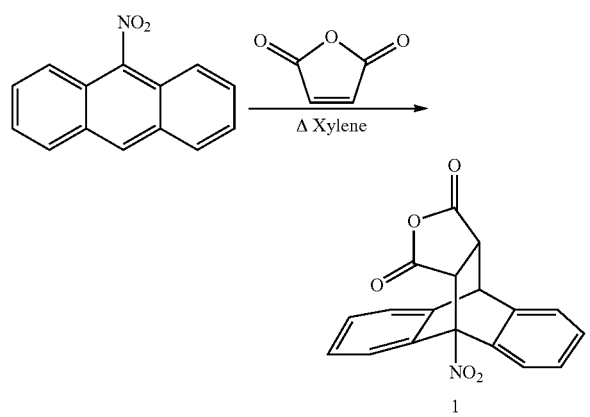

Maleic anhydride (0.46 g, 4.71 mmol) was added to a stirring solution of 9-nitroanthracene (1.03 g, 4.61 mmol) in xylene (25 mL) and the mixture heated under reflux at 140-143° C., for 3-5 days, until all the diene disappeared as indicated on TLC. The reaction mixture was cooled to room temperature before placing on ice while stirring. A precipitate separated out upon cooling. The precipitate was filtered and washed with ice-cold xylene to give the desired Diels-Alder cycloadduct 1, which was used in the next step without further purification. Pale yellow powder. Yield 0.969 g (65%). Mp: 239-240° C. $^1$H NMR (400 MHz, DMSO-$d_6$) δ (ppm) 7.65-7.69 (1H, m), 7.50-7.58 (2H, m), 7.37-7.44 (3H, m), 7.32-7.37 (1H, m), 7.05 (1H, dd, J=7.5, 0.5 Hz), 5.11 (1H, d, J=3.0 Hz), 4.66 (1H, d, J=9.3 Hz), 3.94 (1H, dd, J=9.3, 3.2 Hz). $^{13}$C NMR (400 MHz, DMSO-$d_6$) δ (ppm) 170.32, 168.99, 139.47, 137.17, 136.93, 134.15, 129.49, 129.44, 128.40, 128.17, 126.11, 125.60, 123.37, 120.81, 93.24, 51.14, 49.25, 44.79. $v_{max}$/cm$^{-1}$: 2988, 2969 (C—H stretch), 1781 (C=O stretch), 1556 ($NO_2$ asymmetric), 1361 ($NO_2$ symmetric). m/z: 352 (100%, [M−H+$CH_3$OH]).

General Procedure for the Synthesis of N-Substituted 9-nitro-12,14-dioxo-9,10-dihydro-9,10-[3,4]epipyrroloanthracen-13-yl Derivatives (2-22)

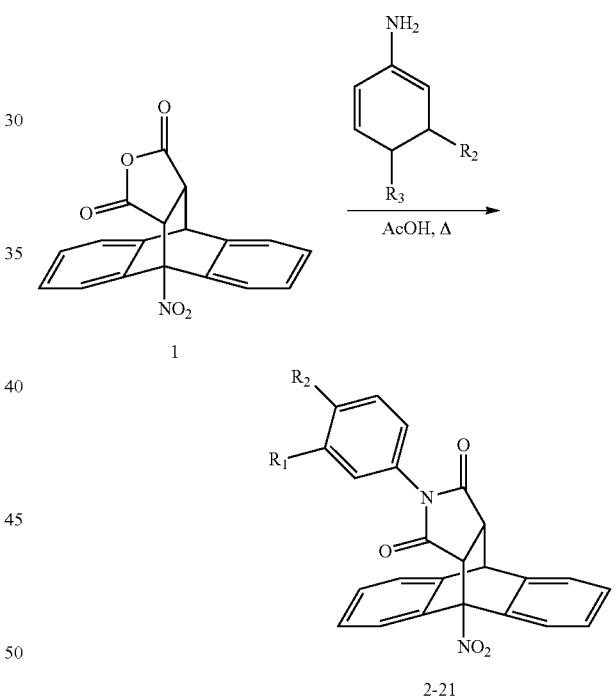

2: $R_1$ = $CO_2H$; $R_2$ = H
3: $R_1$ = $CO_2Et$; $R_2$ = H
4: $R_1$ = F; $R_2$ = H
5: $R_1$ = Cl; $R_2$ = H
6: $R_1$ = $NO_2$; $R_2$ = H
7: $R_1$ = H; $R_2$ = H
8: $R_1$ = H; $R_2$ = $CO_2H$
9: $R_1$ = H; $R_2$ = $CO_2Et$
10: $R_1$ = H; $R_2$ = F
11: $R_1$ = H; $R_2$ = Cl
12: $R_1$ = H; $R_2$ = $NO_2$
13: $R_1$ = H; $R_2$ = I
14: $R_1$ = H; $R_2$ = t-Bu
15: $R_1$ = H; $R_2$ = OMe
16: $R_1$ = H; $R_2$ = $NMe_2$
17: $R_1$ = H; $R_2$ = Me
18: $R_1$ = OMe; $R_2$ = H
19: $R_1$ = $NMe_2$; $R_2$ = H
20: $R_1$ = CN; $R_2$ = H
21: $R_1$ = Me; $R_2$ = H

To a stirring solution of maleic anhydride 9-nitroanthracene cycloadduct (1, 1eg) in glacial acetic acid (10 mL) was placed the respective 3- or 4-substituted aniline (1.2-1.5 equivalents). The mixture was heated under reflux at 120° C. for 2-3 h then cooled to room temperature. De-ionised water was added to the cooled mixture and the resulting precipitate was filtered, washed with de-ionised water and dried under suction to yield the desired product.

3-(9-Nitro-12,14-dioxo-9,10-dihydro-9,10-[3,4]epipyrroloanthracen-13-yl)benzoic acid (2)

$^1$H NMR (400 MHz, acetone-d$_6$) δ (ppm) 7.92-8.00 (1H, m), 7.69-7.77 (2H, m), 7.35-7.52 (7H, m), 7.27 (1H, dt, J=5.2, 1.7 Hz), 7.06-7.13 (1H, m), 6.72-6.80 (1H, m), 5.02-5.08 (1H, m), 4.57-4.65 (1H, m), 3.72-3.79 (1H, m). $^{13}$C NMR (400 MHz, ACETONE-d$_6$) δ (ppm) 174.06 (1 C=O amide), 170.58 (1 C=O amide), 170.10 (1 C=O carboxyl), 130.97, 129.70, 129.12, 128.79, 128.50, 127.99, 127.52, 127.48, 125.48, 124.73, 123.80, 120.56, 92.66 (1 C—NO$_2$ aliphatic), 49.42 (1 C—H aliphatic), 47.91 (1 C—H aliphatic), 45.80 (1 C—H aliphatic). ν$_{max}$/cm$^{-1}$: 3535 (OH stretch), 1705 (C=O stretch), 1551 (NO$_2$ asymmetric), 1366 (NO$_2$ symmetric). m/z: 439 (100%, [M−CH$_3$OH]$^-$). Mp: 268-273° C.

Ethyl 3-(9-nitro-12,14-dioxo-9,10-dihydro-9,10-[3,4]epipyrroloanthracen-13-yl)benzoate (3)

$^1$H NMR (400 MHz, acetone-d$_6$) δ (ppm) 7.95 (1H, dq, J=7.9, 0.9 Hz), 7.68-7.78 (2H, m), 7.35-7.52 (6H, m), 7.14-7.18 (1H, m), 7.08-7.12 (1H, m), 6.76-6.83 (1H, m), 5.07 (1H, d, J=3.4 Hz), 4.62 (1H, d, J=8.8 Hz), 4.34 (2H, q, J=7.1 Hz), 3.76 (1H, dd, J=8.8, 3.1 Hz), 1.37 (3H, t, J=7.1 Hz). $^{13}$C NMR (600 MHz, acetone-d$_6$) δ (ppm) 174.06, 172.93, 164.76, 139.76, 137.58, 137.48, 134.39, 132.23, 131.52, 131.16, 129.46, 129.22, 128.79, 128.49, 127.70, 127.53, 127.47, 125.48, 124.72, 123.81, 120.55, 93.69, 61.02, 49.44, 47.94, 45.78, 13.72. ν$_{max}$/cm$^{-1}$: 2984, 2903 (CH stretch), 1710 (C=O stretch), 1551 (NO$_2$ asymmetric), 1363 (NO$_2$ symmetric). m/z: 469 (20%, M+H), 491 (7%, M+H+Mp: 202-203° C.

13-(3-Chlorophenyl)-9-nitro-9,10-dihydro-9,10-[3,4]epipyrroloanthracene-12,14-dione (4)

$^1$H NMR (400 MHz, DMSO-d$_6$) δ (ppm) 7.71 (1H, d, J=7.2 Hz), 7.61-7.66 (1H, m), 7.31-7.51 (1H, m), 7.06 (1H, d, J=7.1 Hz), 6.40-6.52 (1H, m), 5.07 (1H, d, J=3.0 Hz), 4.49 (1H, d, J=8.8 Hz), 3.69 (1H, dd, J=8.7, 3.2 Hz). $^{13}$C NMR (400 MHz, DMSO-d$_6$) δ (ppm) 174.63, 173.44, 134.30, 133.04, 131.38, 129.29, 128.03, 126.84, 125.83, 123.80, 120.75, 93.74, 69.62, 49.63, 48.01, 45.29. ν$_{max}$/cm$^{-1}$: 3115, 2981, 2966 (CH stretch), 1717 (C=O stretch), 1547 (NO$_2$ asymmetric), 1383 (NO$_2$ symmetric). m/z: 431 (<5%, M+H). Mp: 255-230° C.

13-(3-Fluorophenyl)-9-nitro-9,10-dihydro-9,10-[3,4]epipyrroloanthracene-12,14-dione (5)

$^1$H NMR (400 MHz, dichloromethane-d$_2$) δ (ppm) 7.74 (1H, d, J=6.8 Hz), 7.54 (1H, d, J=7.0 Hz), 7.18-7.46 (8H, m), 6.94-7.16 (2H, m), 6.35 (1H, d, J=7.7 Hz), 6.12-6.31 (1H, m), 4.93 (1H, d, J=3.1 Hz), 4.45 (1H, d, J=9.0 Hz), 3.56 (1H, dd, J=9.0, 3.1 Hz). $^{13}$C NMR (400 MHz, dichloromethane-d$_2$) δ (ppm) 173.73, 172.37, 163.65, 138.96, 137.13, 136.49, 133.93, 130.34, 128.88, 128.66, 127.80, 127.68, 125.36, 124.36, 123.90, 122.24, 120.91, 116.18, 115.97, 114.03, 113.79, 93.42, 49.03, 47.77, 45.99. ν$_{max}$/cm$^{-1}$: 3075 (CH stretch), 3040, 3015, 2973, 2890 (CH stretch), 1706 (C=O stretch), 1551 (NO$_2$ asymmetric), 1383 (NO$_2$ symmetric). m/z: 415% (<5%, M+H). Mp: 241-243° C.

9-Nitro-13-(3-nitrophenyl)-9,10-dihydro-9,10-[3,4]epipyrroloanthracene-12,14-dione (6)

$^1$H NMR (400 MHz, dichloromethane-d$_2$) δ (ppm) 8.15 (1H, ddt, J=8.3, 2.2, 1.2, 1.2 Hz), 7.68-7.78 (1H, m), 7.47-7.59 (2H, m), 7.26-7.46 (6H, m), 7.06-7.16 (1H, m), 6.94 (1H, ddt, J=8.0, 2.1, 1.1, 1.1 Hz), 4.95 (1H, d, J=3.0 Hz), 4.50 (1H, dd, J=8.9, 1.3 Hz), 3.61 (1H, ddd, J=8.9, 3.1, 1.2 Hz). $^{13}$C NMR (600 MHz, dichloromethane-d$_2$) δ (ppm) 173.55, 172.23, 148.41, 138.77, 136.96, 136.39, 133.86, 132.37, 132.01, 130.10, 128.96, 128.80, 127.93, 127.76, 125.41, 124.40, 123.93, 123.72, 121.67, 120.95, 93.42, 49.13, 47.88, 46.04. ν$_{max}$/cm$^{-1}$: 3094, 3080, 3049, 2976, 2971, 2959, 2887, (CH stretch), 1709 (C=O stretch), 1548, 1529 (NO$_2$ asymmetric), 1341 (NO$_2$ symmetric). m/z: 442 (<5%, M+H). Mp: 240-242° C.

9-Nitro-13-phenyl-9,10-dihydro-9,10-[3,4]epipyrroloanthracene-12,14-dione (7)

$^1$H NMR (400 MHz, DMSO-d$_6$) δ (ppm) 7.71 (1H, d, J=7.3 Hz), 7.62-7.67 (1H, m), 7.30-7.50 (9H, m), 7.05 (1H, d, J=7.6 Hz), 6.42-6.47 (2H, m), 5.07 (1H, d, J=2.6 Hz), 4.50 (1H, dd, J=8.8, 1.5 Hz), 3.66 (1H, ddd, J=8.8, 3.0, 1.4 Hz). ν$_{max}$/cm$^{-1}$: 3070, 2972, 2903 (CH stretch), 1713 (C=O stretch), 1550 (NO$_2$ asymmetric), 1387 (NO$_2$ symmetric). m/z: 397 (10%, M+H). Mp: 110-112° C.

4-(9-Nitro-12,14-dioxo-9,10-dihydro-9,10-[3,4]epipyrroloanthracen-13-yl)benzoic acid (8)

$^1$H NMR (400 MHz, acetone-d$_6$) δ (ppm) 7.97 (2H, d, J=8.9 Hz), 7.69-7.78 (1H, m), 7.47-7.51 (1H, m), 7.35-7.45 (4H, m), 7.08-7.12 (1H, m), 6.73 (2H, d, J=8.8 Hz), 5.05-5.08 (1H, m), 4.62 (1H, d, J=8.9 Hz), 3.76 (1H, dd, J=8.9, 3.1 Hz). $^{13}$C NMR (600 MHz, acetone-d$_6$) δ (ppm) 173.91, 172.76, 165.94, 139.77, 137.58, 137.41, 135.70, 134.33, 130.86, 130.08, 128.80, 128.52, 127.53, 127.49, 126.57, 125.47, 124.71, 123.77, 120.54, 93.69, 49.39, 47.89, 45.77. ν$_{max}$/cm$^{-1}$: 3284 (OH stretch), 3076, 2970, 2903 (CH stretch), 1702 (C=O stretch), 1550 (NO$_2$ asymmetric), 1389 (NO$_2$ symmetric). m/z: 439 (100%, M−H). Mp: 340-345° C.

Ethyl 4-(9-nitro-12,14-dioxo-9,10-dihydro-9,10-[3,4]epipyrroloanthracen-13-yl)benzoate (9)

$^1$H NMR (400 MHz, acetone-d$_6$) δ (ppm) 7.92-7.97 (2H, m), 7.68-7.77 (2H, m), 7.47-7.51 (1H, m), 7.36-7.46 (4H, m), 7.10 (1H, d, J=6.1 Hz), 6.70-6.74 (2H, m), 5.07 (1H, d, J=3.1 Hz), 4.62 (1H, d, J=8.9 Hz), 4.32 (2H, q, J=7.1 Hz), 3.76 (1H, dd, J=8.8, 3.0 Hz), 1.33 (3H, t, J=7.1 Hz). $^{13}$C NMR (600 MHz, acetone-d$_6$) δ (ppm) 173.85, 172.73, 139.76, 129.78, 128.79, 128.51, 127.48, 126.61, 125.46, 124.71, 123.77, 120.54, 60.91, 49.39, 47.89, 45.78, 13.65. ν$_{max}$/cm$^{-1}$: 2989 (CH stretch), 1710 (C=O stretch), 1550 (NO$_2$ asymmetric), 1394 (NO$_2$ symmetric). m/z: 469 (10%, M+H). Mp: 255-260° C.

13-(4-Chlorophenyl)-9-nitro-9,10-dihydro-9,10-[3,4]epipyrroloanthracene-12,14-dione (10)

$^1$H NMR (400 MHz, dichloromethane-d$_2$) δ (ppm) 7.70-7.75 (1H, m), 7.52-7.56 (1H, m), 7.37-7.42 (2H, m), 7.31-

7.37 (4H, m), 7.26-7.31 (3H, m), 7.09-7.12 (1H, m), 6.44-6.49 (2H, m), 4.92 (1H, d, J=3.1 Hz), 4.44 (1H, d, J=8.9 Hz), 3.55 (1H, dd, J=8.9, 3.1 Hz). $^{13}$C NMR (600 MHz, dichloromethane-d$_2$) δ (ppm) 173.84, 172.47, 138.96, 137.14, 136.49, 134.80, 133.92, 129.62, 129.29, 128.86, 128.60, 127.76, 127.68, 125.34, 124.34, 120.90, 93.43, 49.02, 45.99. $v_{max}$/cm$^{-1}$: 2981, 2971, 2887 (CH stretch), 1709 (C=O stretch), 1551 (NO$_2$ asymmetric), 1389 (NO$_2$ symmetric). m/z: 431 (<10%, M+H). Mp: 270-273° C.

13-(4-Fluorophenyl)-9-nitro-9,10-dihydro-9,10-[3,4]epipyrroloanthracene-12,14-dione (11)

$^1$H NMR (400 MHz, dichloromethane-d$_2$) δ (ppm) 7.73 (1H, dd, J=6.6, 2.4 Hz), 7.51-7.56 (1H, m), 7.29-7.43 (7H, m), 7.08-7.13 (1H, m), 6.96-7.04 (2H, m), 6.44-6.50 (2H, m), 4.92 (1H, d, J=3.0 Hz), 4.44 (1H, d, J=9.0 Hz), 3.54 (1H, dd, J=8.9, 3.1 Hz). $^{13}$C NMR (400 MHz, dichloromethane-d$_2$) δ (ppm) 174.05, 172.68, 139.00, 137.16, 136.55, 128.86, 128.60, 128.39, 128.30, 127.75, 127.66, 127.06, 125.36, 124.35, 123.90, 120.90, 116.23, 116.00, 93.44, 49.00, 47.74, 45.99. $v_{max}$/cm$^{-1}$: 2981, 2970, 2893 (CH stretch), 1710 (C=O stretch), 1551 (NO$_2$ asymmetric), 1395 (NO$_2$ symmetric). m/z: 415 (<5%, M+H). Mp: 220-225° C.

9-Nitro-13-(4-nitrophenyl)-9,10-dihydro-9,10-[3,4]epipyrroloanthracene-12,14-dione (12)

$^1$H NMR (400 MHz, dichloromethane-d$_2$) δ (ppm) 8.12-8.16 (2H, m), 7.72-7.76 (1H, m), 7.53-7.56 (1H, m), 7.30-7.44 (6H, m), 7.10-7.14 (1H, m), 6.78-6.83 (2H, m), 4.94 (1H, d, J=3.1 Hz), 4.49 (1H, d, J=9.0 Hz), 3.60 (1H, dd, J=9.0, 3.1 Hz). $^{13}$C NMR (400 MHz, dichloromethane-d$_2$) δ (ppm) 170.62 (s), 169.30, 144.68, 136.03, 133.66, 131.07, 126.19, 125.97, 125.11, 124.99, 124.30, 121.62, 121.54, 121.11, 118.17, 90.62, 46.33, 45.06, 43.25. $v_{max}$/cm$^{-1}$: 3121, 3087, 2978, 2855 (CH stretch), 17812 (C=O stretch), 1551, 1521 (NO$_2$ asymmetric), 1344 (NO$_2$ symmetric). m/z: 442 (5%, M+H). Mp: 316-318° C.

13-(4-(tert-Butyl)phenyl)-9-nitro-9,10-dihydro-9,10-[3,4]epipyrroloanthracene-12,14-dione (13)

$^1$H NMR (400 MHz, dichloromethane-d$_2$) δ (ppm) 7.72-7.75 (1H, m), 7.51-7.55 (1H, m), 7.28-7.43 (9H, m), 7.08-7.12 (1H, m), 6.36-6.41 (2H, m), 4.92 (1H, d, J=3.1 Hz), 4.43 (1H, d, J=9.0 Hz), 3.53 (1H, dd, J=8.9, 3.1 Hz), 1.26 (9H, s). $^{13}$C NMR (600 MHz, dichloromethane-d$_2$) δ (ppm) 174.33, 172.92, 152.38, 139.09, 137.23, 136.57, 133.95, 128.82, 128.58, 128.42, 127.72, 127.61, 126.18, 125.90, 125.37, 124.34, 123.89, 120.86, 93.47, 48.98, 47.74, 45.97, 34.65, 30.92. $v_{max}$/cm$^{-1}$: 2981, 2902, 2875 (CH stretch), 1714 (C=O stretch), 1547 (NO$_2$ asymmetric), 1392 (NO$_2$ symmetric). m/z: 453 (65%, M+H). Mp: 238-240° C.

13-(4-Iodophenyl)-9-nitro-9,10-dihydro-9,10-[3,4]epipyrroloanthracene-12,14-dione (14)

$^1$H NMR (400 MHz, DMSO-d$_6$) δ (ppm) 7.66-7.77 (4H, m), 7.59-7.65 (1H, m), 7.30-7.49 (6H, m), 7.05 (1H, d, J=7.5 Hz), 6.23-6.32 (2H, m), 5.06 (1H, d, J=2.6 Hz), 4.48 (1H, dd, J=8.8, 2.0 Hz), 3.66 (1H, ddd, J=8.7, 3.0, 2.0 Hz). $^{13}$C NMR (400 MHz, DMSO-d$_6$) δ (ppm) 174.65, 173.44, 139.89, 138.50, 137.60, 137.47, 134.20, 131.46, 129.28, 128.91, 127.94, 125.90, 125.41, 123.73, 120.73, 95.62, 93.74, 49.59, 47.97, 45.28. $v_{max}$/cm$^{-1}$: 2968, 2901 (CH stretch), 1706 (1 C=O stretch), 1550 (NO$_2$ asymmetric), 1387 (NO$_2$ symmetric). m/z: 523 (<5%, M+H). Mp: 301-306° C.

13-(4-Methoxyphenyl)-9-nitro-9,10-dihydro-9,10-[3,4]epipyrroloanthracene-12,14-dione (15)

$^1$H-NMR (600 MHz, DMSO-d$_6$) δ (ppm): 7.68 (1H, d, J=1.0 Hz), 7.62-7.64 (1H, m), 7.35-7.41 (5H, m), 7.04 (1H, d, J=7.7 Hz), 6.88 (2H, d, J=8.9 Hz, aniline p-substitution), 6.33 (2H, d, J=9.0 Hz, aniline p-substitution), 5.04 (1H, s), 4.45 (1H, d, J=8.8 Hz), 3.71 (3H, s, methyl), 3.62 (1H, d, J=8.8 Hz). $^{13}$C-NMR (600 MHz, DMSO-d$_6$) δ (ppm): 174.53 (C=O), 173.33 (C=O), 159.18 (aniline C—OMe), 139.42, 137.11, 136.99, 133.72, 128.66, 128.33, 127.57 (2C, aniline p-substitution), 127.39, 127.27, 125.33, 124.79, 123.75, 123.20, 120.12, 114.21 (2C, aniline p-substitution), 93.19 (aliphatic CH), 55.82 (methyl), 48.90 (aliphatic CH), 47.65 (aliphatic CH), 44.21 (aliphatic CH). $v_{max}$/cm$^{-1}$: 3073, 2960 (C—H stretch), 1700 (C=O stretch), 1548 (NO$_2$ asymmetric), 1395 (NO$_2$ symmetric), 1255 (C—N stretch), 1192, 1166 (C—O stretch). m/z: 427.3 (38%, [M+H]$^+$; C$_{26}$H$_{18}$N$_2$O$_6$ predicted=426.43). Mp: 250-254° C.

13-(4-(Dimethylamino)phenyl)-9-nitro-9,10-dihydro-9,10-[3,4]epipyrroloanthracene-12,14-dione (16)

$^1$H-NMR (600 MHz, DMSO-d$_6$) δ (ppm): 7.68 (1H, d, J=8.4 Hz), 7.60-7.61 (1H, m), 7.37-7.39 (5H, m), 7.02 (1H, d, J=7.6 Hz), 6.57 (2H, d, J=9.1 Hz, aniline p-substitution), 6.19 (2H, d, J=8.9 Hz, aniline p-substitution), 5.01 (1H, s), 4.42 (1H, d, J=8.8 Hz), 3.57 (1H, d, J=11.9 Hz), 2.85 (6H, s, dimethyl). $^{13}$C-NMR (600 MHz, DMSO-d$_6$) δ (ppm): 174.75 (C=O), 173.54 (C=O), 150.19 (C—N-dimethyl), 139.47, 137.11, 137.04, 133.72, 128.60, 128.25, 127.34, 127.20, 126.82 (4C), 125.29, 124.73, 123.18, 120.08 (aniline p-substitution), 119.42 (aniline p-substitution), 111.81 (2C, aniline p-substitution), 93.20 (aliphatic CH), 48.90 (aliphatic CH), 47.95 (aliphatic CH), 44.90 (aliphatic CH). $v_{max}$/cm$^{-1}$: 3040, 2890 (C—H stretch), 1702 (C=O stretch), 1545 (NO$_2$ asymmetric), 1362 (NO$_2$ symmetric), 1170 (C—N stretch). m/z: 440.4 (100%, [M+H]$^+$; C$_{26}$H$_{21}$N$_3$O$_4$ predicted=439.47). Melting Point: 265-266° C.

9-Nitro-13-(p-tolyl)-9,10-dihydro-9,10-[3,4]epipyrroloanthracene-12,14-dione (17)

Mp=258-262° C.; $^1$H NMR (400 MHz, DMSO-d6) δ (ppm): 7.69 (1H, dd, J=1.76, J=0.92 Hz), 7.64-7.62 (1H, m), 7.41-7.35 (5H, m), 7.13 (2H, d, J=8.08), 7.04 (1H, d, J=7.4), 6.32 (2H, dd, J=1.72, J=3.92 Hz), 5.05 (1H, d, J=3.04 Hz), 4.47 (1H, d, J=8.72 Hz), 3.63 (1H, dd, J=3.12, J=2.2 Hz), 2.25 (3H, s); $^{13}$C NMR (400 MHz, DMSO-d6) δ (ppm): 175.02, 173.82, 140.08, 138.99, 137.68, 137.56, 134.27, 129.99 (2C), 129.26, 128.94, 127.99, 127.89, 126.70 (2C), 125.92, 125.41, 123.78, 120.72, 93.76, 49.51, 48.01, 45.68, 21.21; IR vmax/cm-1: 2988 (C—H stretch), 1715 (C=O stretch), 1550 (NO$_2$ asymmetric stretch), 1326 (NO$_2$ symmetric stretch) 1458, 1387 (C—H bend), 1183 (C—N stretch); m/z: 411.3 (2.5%, [M+H]+); predicted mass of C$_{25}$H$_{18}$N$_2$O$_4$=410.45.

13-(3-Methoxyphenyl)-9-nitro-9,10-dihydro-9,10-[3,4]epipyrroloanthracene-12,14-dione (18)

$^1$H-NMR (600 MHz, DMSO-d$_6$) δ (ppm): 7.69 (1H, d, J=7.4 Hz), 7.62-7.64 (1H, m), 7.23-7.47 (6H, m), 7.04 (1H, d, J=12.2 Hz), 6.91 (1H, d, J=2.6 Hz), 6.06 (1H, d, J=7.9 Hz), 5.82 (1H, s), 5.04 (1H, s), 4.46 (1H, d, J=10.1 Hz), 3.65 (3H, s, methyl), 3.64 (1H, d, J=9.5 Hz). $^{13}$C-NMR (600 MHz, DMSO-d$_6$) δ (ppm): 174.22 (C=O), 173.02 (C=O), 159.38 (aniline C—OMe), 139.35, 137.11, 136.92, 133.72, 132.31, 129.81, 128.65, 128.34, 127.39, 127.29, 125.36, 124.81, 123.23, 120.13 (aniline), 118.65 (aniline), 114.49 (aniline), 112.10 (aniline), 93.18 (aliphatic CH), 55.82 (methyl), 48.75 (aliphatic CH), 47.90 (aliphatic CH), 44.89 (aliphatic CH). ν$_{max}$/cm$^{-1}$: 3065, 2998 (C—H stretch), 1714 (C=O stretch), 1549 (NO$_2$ asymmetric), 1386 (NO$_2$ symmetric), 1244 (C—N stretch), 1199, 1153 (C—O stretch). m/z: 449.3 (36%, [M+Na]; C$_{25}$H$_{18}$N$_2$O$_5$ predicted=426.43). Melting Point: 262-266° C.

13-(3-(Dimethylamino)phenyl)-9-nitro-9,10-dihydro-9,10-[3,4]epipyrroloanthracene-12,14-dione (19)

$^1$H-NMR (400 MHz, DMSO-d$_6$) δ (ppm): 7.68 (1H, d, J=8.5 Hz), 7.62-7.64 (1H, m), 7.35-7.46 (6H, m), 7.10 (1H, t, J=8.3 Hz), 7.04 (1H, d, J=7.1 Hz), 6.65 (1H, d, J=10.4 Hz), 5.78 (1H, d, J=8.6 Hz), 5.39 (1H, s), 5.03 (1H, s), 4.46 (1H, d, J=8.7 Hz), 2.77 (6H, s, dimethyl). $^{13}$C-NMR (600 MHz, DMSO-d$_6$) δ (ppm): 174.61 (2C, C=O), 151.13 (aniline C—N-dimethyl), 139.85 (2C), 138.70 (2C), 137.47 (aniline), 132.63 (aniline), 128.81 (2C), 127.82 (4C), 127.56 (2C), 120.25 (aniline), 112.95 (aniline), 110.48 (aniline), 93.71 (aliphatic CH), 45.10 (aliphatic CH), 49.04 (aliphatic CH), 47.96 (aliphatic CH), 44.83 (2C, dimethyl). ν$_{max}$/cm$^{-1}$: 2968, 2948 (C—H stretch), 1710 (C=O stretch), 1551, (NO$_2$ asymmetric), 1393 (NO$_2$ symmetric), 1246 (C—N stretch). Melting Point: 213-215° C.

3-(9-Nitro-12,14-dioxo-9,10-dihydro-9,10-[3,4] epipyrroloanthracen-13-yl)benzonitrile (20)

$^1$H-NMR (600 MHz, DMSO-d6) δ (ppm): 7.84 (1H, d, J=0.5 Hz, benzonitrile), 7.70 (2H, d, J=1.0 Hz, benzonitrile), 7.58-7.62 (1H, m, benzonitrile), 7.40-7.49 (5H, m), 7.05 (1H, d, J=3.8 Hz), 6.89-6.90 (1H, m), 6.77-6.78 (1H, m), 5.07 (1H, s), 4.51 (1H, d, J=8.8 Hz), 3.72 (1H, d, J=3.1 Hz); $^{13}$C-NMR (600 MHz, DMSO-d6) δ (ppm): 173.94 (C=O), 172.75 (C=O), 139.20 (benzene C), 137.03 (benzene C), 136.77 (benzene C), 133.66 (benzene C), 132.72 (aniline), 131.89 (aniline), 131.26 (aniline), 130.70 (aniline), 129.59 (aniline), 128.73, 128.45, 127.46, 127.39, 125.40, 124.89, 123.21, 120.19, 117.47 (aniline C≡N), 112.00 (aniline C-cyano), 93.16 (aliphatic C—H), 49.02 (aliphatic C—H), 47.63 (aliphatic C—H), 44.42 (aliphatic CH). ν$_{max}$/cm$^{-1}$: 3064, 2995 (C—H stretch), 2231 (C≡N stretch), 1715 (C=O stretch), 1547 (NO$_2$ asymmetric), 1386 (NO$_2$ symmetric), 1177 (C—N stretch). Melting Point: 310-311° C.

9-Nitro-13-(m-tolyl)-9,10-dihydro-9,10-[3,4]epipyrroloanthracene-12,14-dione (21)

Mp=209-211° C.; $^1$H NMR (400 MHz, DMSO-d6) δ (ppm): 7.70 (1H, d, J=6.63 Hz), 7.63-7.65 (1H, m), 7.36-7.47 (5H, m), 7.22 (1H, t, J=7.72 Hz), 7.14 (1H, d, J=7.68), 7.05 (1H, d, J=7.48 Hz), 6.22 (2H, t, J=8.00 Hz), 5.06 (1H, d, J=3.00 Hz), 4.48 (1H, d, J=8.72 Hz), 3.65 (1H, dd, J=3.12 Hz, J=2.32 Hz), 2.21 (3H, s); $^{13}$C NMR (400 MHz, DMSO-d6) δ (ppm): 175.00, 173.80, 139.98, 139.09, 137.70, 137.55, 134.30, 131.83, 130.00, 129.37, 129.26, 128.95, 128.00, 127.91, 127.48, 125.97, 125.42, 124.10, 123.83, 120.74, 93.76, 49.51, 48.05, 45.88, 21.24; IR ν$_{max}$/cm-1: 1710 (C=O stretch), 1545 (NO$_2$ asymmetric stretch), 1360 (NO$_2$ symmetric stretch) 1459, 1383 (C—H bend), 1179 (C—N stretch).

Heterocyclic Analogues (22-24)

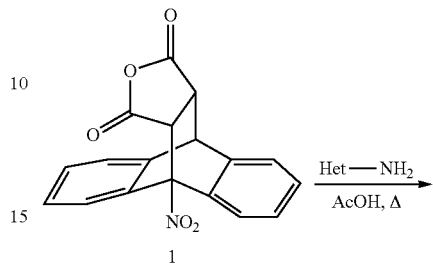

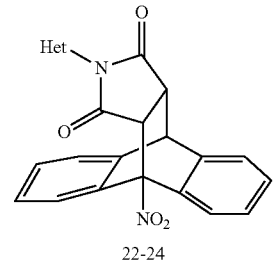

Ethyl 3-(9-nitro-12,14-dioxo-9,10-dihydro-9,10-[3, 4]epipyrroloanthracen-13-yl)-pyrazole-4-carboxylate (22)

$^1$H-NMR (400 MHz, DMSO-d$_6$) δ (ppm): 8.37 (2H, s, pyrazole), 7.69-7.72 (2H, m), 7.56-7.59 (2H, m), 7.33-7.41 (4H, m), 4.64-4.66 (2H, m), 4.09 (1H, q, J=7.0 Hz), 3.83 (1H, d, J=12.1 Hz), 3.76 (1H, d, J=11.4 Hz), 1.91 (3H, s, methyl). $^{13}$C-NMR (600 MHz, DMSO-d$_6$) δ (ppm): 173.23 (C=O), 172.04 (C=O), 161.51 (O=C—O), 139.03 (2C), 137.31 (2C), 136.71 (pyrazole), 134.32 (pyrazole), 128.58 (2C), 127.36 (4C), 125.40 (2C), 93.84 (aliphatic CH), 93.06 (pyrazole), 59.83 (aliphatic pyrazole CH$_2$), 48.63 (aliphatic CH), 47.11 (aliphatic CH), 44.41 (aliphatic CH), 14.02 (methyl). ν$_{max}$/cm$^{-1}$: 3013, 2948 (C—H stretch), 1710 (C=O stretch), 1607 (N—H stretch), 1551 (NO$_2$ asymmetric), 1393 (NO$_2$ symmetric), 1246 (C—N stretch), 1199, 1166 (C—O stretch). m/z: 457.1 (100%, [M–H]$^-$; C$_{24}$H$_{18}$N$_4$O$_6$ predicted=458.43). Melting Point: 128-130° C.

9-Nitro-13-(1,2,4-triazol-4-yl)-9,10-dihydro-9,10-[3,4]epipyrroloanthracene-12,14-dione (23)

$^1$H-NMR (400 MHz, DMSO-$d_6$) δ (ppm): 7.80 (2H, s, triazole), 7.72 (1H, d, J=8.2 Hz), 7.45-7.51 (6H, m), 7.09 (1H, d, J=7.3 Hz), 5.15 (1H, s), 4.59 (1H, d, J=8.7 Hz), 3.89 (1H, d, J=11.6 Hz). $^{13}$C-NMR (400 MHz, DMSO-$d_6$) δ (ppm): 170.60 (C=O), 169.41 (C=O), 141.90 (2C, triazole), 139.14 (benzene C), 137.26 (benzene C), 136.73 (benzene C), 133.90 (benzene C), 129.58, 129.50, 128.43, 128.23, 126.11, 125.68, 123.63, 120.94, 93.61 (aliphatic CH), 48.12 (aliphatic CH), 46.42 (aliphatic CH), 45.02 (aliphatic CH). $v_{max}$/cm$^{-1}$: 3089, 2974 (C—H stretch), 1751 (C=O stretch), 1551, (NO$_2$ asymmetric), 1459 (C=N stretch), 1360 (NO$_2$ symmetric), 1291 (C—N stretch), 1173 (C—N stretch). Melting Point: 314-315° C.

3-(12,14-Dioxo-9,10-dihydro-9,10-[3,4]-epipyrrolanthracene-13-yl)-1H-1,2,4-triazole-5-carboxylic acid (24)

Mp=248-252° C.; $^1$H NMR (600 MHz, CDCl$_3$) δ (ppm): 7.36-7.41 (2H, m), 7.29-7.32 (2H, m), 7.24 (1H, s), 7.17-7.20 (2H, m), 7.14-7.16 (1H, m), 4.88 (2H, t, J=1.56 Hz), 3.43 (2H, t, J=1.74); $^{13}$C NMR (600 MHz, CDCl$_3$) δ (ppm): 174.26, 170.43, 141.16, 140.61, 138.27, 138.07, 127.76, 127.40, 127.15, 126.94, 125.20, 125.07, 124.40, 124.35, 47.99, 47.95, 45.65, 45.42; $v_{max}$/cm-1: 1718 (C=O stretch), 1475 (C—H bend), 1188 (C—H bend).

9,10-Dihydro-9,10-[3,4]furanoanthracene-12,14-dione (25)

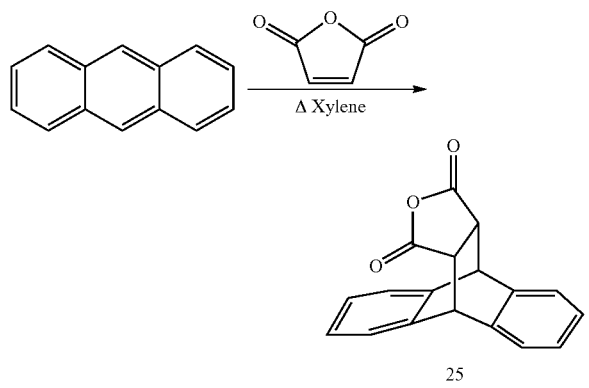

Maleic anhydride (1 g, 102 mmol) was added to a stirring solution to anthracene (1.82 g, 102 mmol) in xylene (25 mL) and the mixture was heated under reflux at 140-143° C. until all the diene disappeared as indicated on TLC. The reaction mixture was cooled to room temperature before placing on ice while stirring. The precipitate was filtered, washed with ice-cold xylene to give the desired Diels-Alder cycloadduct 25 as sand-coloured prisms. The cycloadduct was used in the next step without further purification. Yield 2.69 g (92%). Mp: 259-260° C. $^1$H NMR (400 MHz, acetone-$d_6$) δ (ppm) 7.47-7.51 (2H, m), 7.33-7.38 (2H, m), 7.17-7.22 (4H, m), 4.89-4.92 (2H, m), 3.73-3.75 (2H, m). $^{13}$C NMR (400 MHz, acetone-$d_6$) δ (ppm) 171.22, 141.51, 139.41, 127.23, 126.79, 125.09, 124.48, 48.24, 45.29. $v_{max}$/cm$^{-1}$: 3077, 3026, 2970 (C—H stretch), 1782 (C=O stretch). m/z: 307 (100%, [M–H+CH$_3$OH]).

General Procedure for the Synthesis of N-Substituted 12,14-dioxo-9,10-dihydro-9,10-[3,4]epipyrroloanthracen-13-yl Derivatives (26-45)

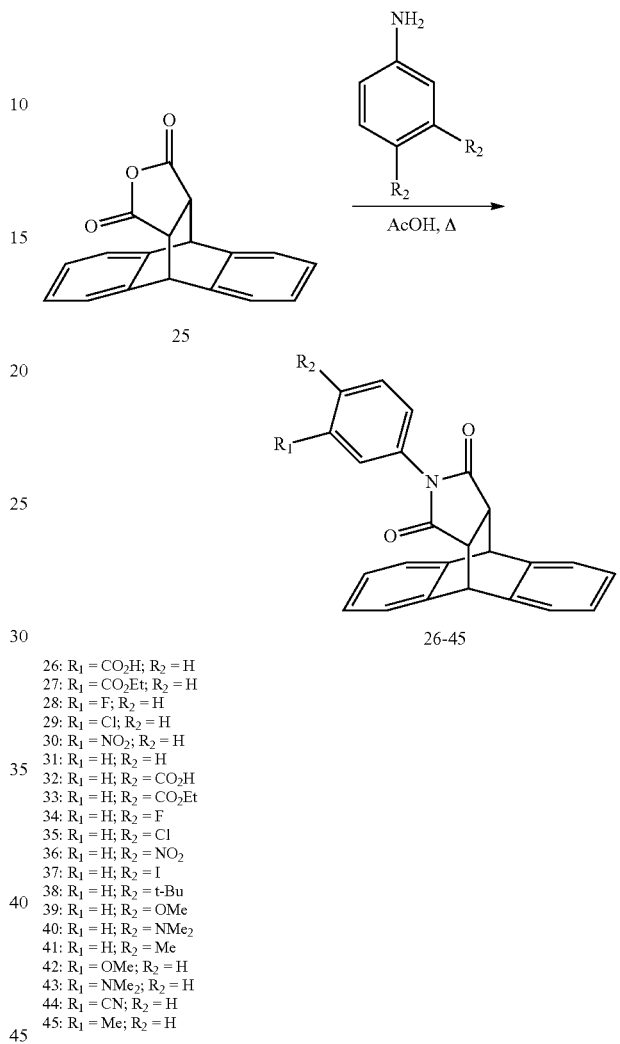

26: R$_1$ = CO$_2$H; R$_2$ = H
27: R$_1$ = CO$_2$Et; R$_2$ = H
28: R$_1$ = F; R$_2$ = H
29: R$_1$ = Cl; R$_2$ = H
30: R$_1$ = NO$_2$; R$_2$ = H
31: R$_1$ = H; R$_2$ = H
32: R$_1$ = H; R$_2$ = CO$_2$H
33: R$_1$ = H; R$_2$ = CO$_2$Et
34: R$_1$ = H; R$_2$ = F
35: R$_1$ = H; R$_2$ = Cl
36: R$_1$ = H; R$_2$ = NO$_2$
37: R$_1$ = H; R$_2$ = I
38: R$_1$ = H; R$_2$ = t-Bu
39: R$_1$ = H; R$_2$ = OMe
40: R$_1$ = H; R$_2$ = NMe$_2$
41: R$_1$ = H; R$_2$ = Me
42: R$_1$ = OMe; R$_2$ = H
43: R$_1$ = NMe$_2$; R$_2$ = H
44: R$_1$ = CN; R$_2$ = H
45: R$_1$ = Me; R$_2$ = H

Maleic anhydride anthracene cycloadduct (25, leg), and the appropriate substituted 3- or 4-substituted aniline (1.2-1.5 eq) were refluxed in glacial acetic acid (10 mL) between 1-5 h then cooled to room temperature. De-ionised water (25-40 mL) was added which resulted in a precipitate. This was filtered, washed with ice-cold de-ionised water and dried.

3-(12,14-Dioxo-9,10-dihydro-9,10-[3,4]epipyrroloanthracen-13-yl)benzoic acid (26)

$^1$H NMR (400 MHz, acetone-$d_6$) δ (ppm) 7.93-7.97 (1H, m), 7.52 (2H, dd, J=5.4, 3.3 Hz), 7.41-7.48 (2H, m), 7.28-7.35 (4H, m), 7.21 (5H, ddd, J=5.4, 3.3, 2.0 Hz), 6.73-6.79 (1H, m), 4.88-4.91 (2H, m), 3.47 (2H, dd, J=2.1, 1.3 Hz). $^{13}$C NMR (400 MHz, ACETONE-$d_6$) δ (ppm) 175.60, 165.77, 141.99, 139.65, 131.12, 129.34, 128.93, 128.10, 126.84, 126.60, 125.00, 124.37, 47.23, 45.82. $v_{max}$/cm$^{-1}$:3321 (OH stretch), 1704 (C=O stretch), 1594 (NO$_2$ asymmetric), 1385 (NO$_2$ symmetric). m/z:394 (100%, M–H). Mp: 285-288° C.

Ethyl 3-(12,14-dioxo-9,10-dihydro-9,10-[3,4]epipyrroloanthracen-13-yl)benzoate (27)

$^1$H NMR (400 MHz, acetone-d$_6$) δ (ppm) 7.89-7.96 (1H, m), 7.49-7.55 (2H, m), 7.45 (1H, t, J=7.9 Hz), 7.30-7.37 (2H, m), 7.15-7.26 (6H, m), 6.76-6.82 (1H, m), 4.89 (2H, t, J=1.5 Hz), 4.33 (2H, q, J=7.1 Hz), 3.47 (2H, dd, J=2.1, 1.3 Hz), 1.36 (3H, t, J=7.1 Hz) $^{13}$C NMR (600 MHz, acetone-d$_6$) δ (ppm) 175.63, 164.90, 131.29, 129.12, 129.02, 127.83, 126.84, 126.61, 125.01, 124.37, 60.94, 47.24, 45.81, 13.73. $v_{max}$/cm$^{-1}$: 3070, 3042, 2992 (CH stretch), 1718, 1703 (C=O stretch). m/z: 424 (15%, M+H). Mp: 205-207° C.

13-(3-fluorophenyl)-9,10-dihydro-9,10-[3,4]epipyrroloanthracene-12,14-dione (28)

$^1$H NMR (400 MHz, dichloromethane-d$_2$) δ (ppm) 7.40-7.47 (2H, m), 7.17-7.35 (8H, m), 6.97-7.05 (1H, m), 6.29-6.36 (1H, m), 6.24 (1H, dt, J=9.2, 2.2 Hz), 4.83-4.89 (2H, m), 3.35-3.41 (2H, m). $^{13}$C NMR (400 MHz, dichloromethane-d$_2$) δ (ppm) 175.60, 163.67, 161.22, 141.40, 139.01, 133.08, 132.98, 130.27, 130.19, 127.18, 126.83, 125.07, 124.38, 122.42, 115.81, 115.60, 114.15, 113.91, 47.13, 45.89. $v_{max}$/cm$^{-1}$: 3083 (CH stretch), 3041 (CH stretch), 3020 (CH stretch), 2974 (CH stretch), 1702 (C=O stretch). m/z: 370 (<5%, M+H). Mp: 228-230° C.

13-(3-chlorophenyl)-9,10-dihydro-9,10-[3,4]epipyrroloanthracene-12,14-dione (29)

$^1$H NMR (400 MHz, DMSO-d$_6$) δ (ppm) 7.49-7.54 (2H, m), 7.36-7.45 (2H, m), 7.30-7.34 (2H, m), 7.17-7.25 (4H, m), 6.42-6.49 (2H, m), 4.87 (2H, s), 3.42 (2H, d, J=1.3 Hz). $^{13}$C NMR (400 MHz, DMSO-d$_6$) δ (ppm) 176.24, 142.05, 139.86, 133.63, 133.46, 131.21, 129.15, 127.22, 126.98, 125.95, 125.38, 124.98, 47.29, 45.44. $v_{max}$/cm$^{-1}$: 3077 (CH stretch), 2960 (CH stretch), 1708 (C=O stretch). m/z: 386 (<5%, M+H). Mp: 238-240° C.

13-(3-nitrophenyl)-9,10-dihydro-9,10-[3,4]epipyrroloanthracene-12,14-dione (30)

$^1$H NMR (400 MHz, dichloromethane-d$_2$) δ (ppm) 8.11-8.15 (1H, m), 7.42-7.52 (3H, m), 7.31-7.38 (3H, m), 7.19-7.27 (4H, m), 6.92 (1H, ddd, J=7.9, 2.0, 1.1 Hz), 4.88 (2H, s), 3.40-3.44 (2H, m). $^{13}$C NMR (600 MHz, dichloromethane-d$_2$) δ (ppm) 175.41, 148.40, 141.19, 138.89, 132.65, 132.54, 129.91, 127.30, 126.90, 125.09, 124.41, 123.36, 121.77, 47.21, 45.93. $v_{max}$/cm$^{-1}$: 3081, 3048, 3011, 2957 (CH stretch), 1710 (C=O stretch), 1530 (NO$_2$ asymmetric), 1341 (NO$_2$ symmetric). m/z: 397 (<5%, M+H). Mp: 282-285° C.

13-phenyl-9,10-dihydro-9,10-[3,4]epipyrroloanthracene-12,14-dione (31)

$^1$H NMR (400 MHz, DMSO-d$_6$) δ (ppm) 7.51 (2H, dd, J=5.3, 3.3 Hz), 7.28-7.36 (5H, m), 7.21 (4H, ddd, J=8.1, 5.1, 3.2 Hz), 6.37-6.47 (2H, m), 4.86 (2H, s), 3.41 (2H, s), 1.91 (1H, d, J=0.5 Hz). $^{13}$C NMR (400 MHz, acetone-d6) δ (ppm) 175.66 (2C=O amide), 171.39 (1C carboxyl), 129.97, 126.62, 125.01, 124.37, 47.21 (2C—H aliphatic), 45.83 (2C—H aliphatic). $v_{max}$/cm$^{-1}$: 3069, 3038, 2969 (CH stretch), 1710 (C=O stretch). m/z: 352 (<5%, M+H). Mp: 211-215° C.

4-(12,14-dioxo-9,10-dihydro-9,10-[3,4]epipyrroloanthracen-13-yl)benzoic acid (32)

$^1$H NMR (400 MHz, acetone-d$_6$) δ (ppm) 7.95 (2H, d, J=8.8 Hz), 7.50-7.54 (2H, m), 7.31-7.35 (2H, m), 7.19-7.23 (4H, m), 6.72 (2H, d, J=8.6 Hz), 4.89 (2H, d, J=1.6 Hz), 3.47 (2H, dd, J=2.0, 1.4 Hz). $^{13}$C NMR (400 MHz, acetone-d$_6$) δ (ppm) 175.66, 171.39, 129.97, 126.62, 125.01, 124.37, 47.21, 45.83. $v_{max}$/cm$^{-1}$: 3283 (OH stretch), 3020 (CH stretch), 2972 (CH stretch), 1698 (C=O stretch), 1105 (C—O stretch). m/z: 394 (100%, M–H). Mp: 352-358° C.

Ethyl 4-(12,14-dioxo-9,10-dihydro-9,10-[3,4]epipyrroloanthracen-13-yl)benzoate (33)

$^1$H NMR (400 MHz, acetone-d$_6$) δ (ppm) 7.89-7.98 (2H, m), 7.45-7.56 (2H, m), 7.28-7.38 (2H, m), 7.16-7.24 (4H, m), 6.67-6.76 (2H, m), 4.78-4.99 (2H, m), 4.32 (2H, q, J=7.1 Hz), 3.47 (2H, dd, J=2.0, 1.4 Hz), 1.33 (3H, t, J=7.1 Hz). $^{13}$C NMR (400 MHz, acetone-d$_6$) δ (ppm) 175.42, 165.09, 141.95, 139.62, 129.65, 126.85, 126.67, 126.61, 124.99, 124.37, 60.86, 47.20, 45.82, 13.67. $v_{max}$/cm$^{-1}$: 2954 (CH stretch), 1707 (C=O stretch). m/z: 424 (50%, M+H). Mp: 220-222° C.

13-(4-fluorophenyl)-9,10-dihydro-9,10-[3,4]epipyrroloanthracene-12,14-dione (34)

$^1$H NMR (400 MHz, dichloromethane-d$_2$) δ (ppm) 7.40-7.46 (2H, m), 7.29-7.34 (3H, m), 7.17-7.24 (5H, m), 6.94-7.02 (2H, m), 6.42-6.49 (2H, m), 4.82-4.88 (2H, m), 3.38-3.43 (2H, m), 3.35-3.38 (2H, m), 2.05 (1H, s). $^{13}$C NMR (400 MHz, dichloromethane-d$_2$) δ (ppm) 175.93, 141.41, 139.05, 128.52, 128.43, 127.12, 126.80, 125.05, 124.37, 116.07, 115.84, 47.10, 45.88. $v_{max}$/cm$^{-1}$: 2975, 2891 (CH stretch), 1708 (C=O stretch). m/z: 370 (<5%, M+H). Mp: 250-253° C.

13-(4-chlorophenyl)-9,10-dihydro-9,10-[3,4]epipyrroloanthracene-12,14-dione (35)

$^1$H NMR (400 MHz, dichloromethane-d$_2$) δ (ppm) 7.37-7.48 (2H, m), 7.10-7.37 (9H, m), 6.40-6.49 (2H, m), 4.85 (2H, s), 3.31-3.41 (2H, m). $^{13}$C NMR (MHz, dichloromethane-d$_2$) δ (ppm) 175.71, 141.38, 139.00, 134.41, 130.24, 129.16, 127.86, 127.13, 126.80, 125.04, 124.36, 47.10, 45.88. $v_{max}$/cm$^{-1}$: 2981, 2973, 2885 (CH stretch), 1702 (C=O stretch). m/z: 386 (<5%, M+H). Mp: 275-278° C.

13-(4-nitrophenyl)-9,10-dihydro-9,10-[3,4]epipyrroloanthracene-12,14-dione (36)

$^1$H NMR (400 MHz, dichloromethane-d$_2$) δ (ppm) 8.09-8.18 (2H, m), 7.37-7.49 (2H, m), 7.28-7.36 (2H, m), 7.14-7.25 (4H, m), 6.76-6.84 (2H, m), 4.88 (1H, s), 4.83 (1H, s), 3.48-3.65 (1H, m), 3.36-3.48 (2H, m). $^{13}$C NMR (600 MHz, dichloromethane-d$_2$) δ (ppm) 175.25, 170.61, 147.24, 141.21, 140.77, 138.88, 138.50, 137.15, 127.61, 127.25, 127.15, 127.07, 126.90, 125.15, 125.06, 124.40, 124.18, 48.04, 47.19, 45.92, 45.43. $v_{max}$/cm$^{-1}$: 3121, 3082, 3017, 2973, 2860 (CH stretch), 1708 (C=O stretch), 1522 (NO$_2$ asymmetric), 1344 (NO$_2$ symmetric). m/z: 397 (<10%, M+H). Mp: 265-268° C.

13-(4-iodophenyl)-9,10-dihydro-9,10-[3,4]epipyrroloanthracene-12,14-dione (37)

$^1$H NMR (400 MHz, DMSO-d$_6$) δ (ppm) 7.68-7.75 (2H, m), 7.47-7.53 (2H, m), 7.26-7.32 (2H, m), 7.19 (4H, dd, J=5.1, 3.5 Hz), 6.23-6.30 (2H, m), 4.86 (2H, s), 3.40 (2H, s). $^{13}$C NMR (400 MHz, DMSO-d$_6$) δ (ppm) 176.23, 142.12, 139.81, 138.35, 132.01, 129.03, 127.22, 126.95, 125.31, 124.94, 95.17, 47.24, 45.41. ν$_{max}$/cm$^{-1}$: 2973 (CH stretch), 1700 (C=O stretch). m/z: 478 (<5%, M+H). Mp: 303-307° C.

13-(4-(tert-utyl)phenyl)-9,10-dihydro-9,10-[3,4] epipyrroloanthracene-12,14-dione (38)

$^1$H NMR (400 MHzdichloromethane-d$_2$) δ (ppm) 7.43 (2H, dd, J=5.4, 3.2 Hz), 7.29-7.34 (4H, m), 7.17-7.25 (5H, m), 6.35-6.40 (2H, m), 4.84-4.86 (2H, m), 3.36 (2H, dd, J=2.1, 1.3 Hz), 1.26 (9H, s). $^{13}$C NMR (600 MHz, dichloromethane-d$_2$) δ (ppm) 176.14, 151.98, 141.54, 139.10, 129.06, 127.06, 126.74, 126.03, 125.05, 124.32, 47.10, 45.89, 34.60, 30.94. ν$_{max}$/cm$^{-1}$: 2963, 2903, 2868 (CH stretch), 1707 (C=O stretch). m/z: 408 (65%, M+H). Mp: 268-271° C.

13-(4-Methoxyphenyl)-9,10-dihydro-9,10-[3,4] epipyrroloanthracene-12,14-dione (39)

$^1$H-NMR (400 MHz, DMSO-d$_6$) δ (ppm): 7.50 (2H, q, J=5.4 Hz), 7.29 (2H, q, J=5.4 Hz), 7.20-7.22 (4H, m), 6.87 (2H, d, J=9.1 Hz, aniline p-substitution), 6.33 (2H, d, J=8.9 Hz, aniline p-substitution), 4.85 (2H, s), 3.71 (3H, s, methyl), 3.38 (2H, s). $^{13}$C-NMR (600 MHz, DMSO-d$_6$) δ (ppm): 176.09 (2C, C=O), 158.95 (aniline C—OMe), 141.61 (2C), 139.29 (2C), 127.66 (2C, aniline p-substitution), 126.54 (2C), 126.30 (2C), 124.73 (2C), 124.30 (2C), 123.76, 114.06 (2C, aniline p-substitution), 55.82 (methyl), 46.01 (2C, aliphatic CH), 44.42 (2C, aliphatic CH). ν$_{max}$/cm$^{-1}$: 3011, 2948 (C—H stretch), 1710 (C=O stretch), 1509 (C=C aromatic ring stretch), 1246 (C—N stretch), 1199, 1166 (C—O stretch). m/z: 404.3 (25%, [M+Na]$^+$; C$_{26}$H$_{16}$NO$_3$ predicted mass 381.43). Melting Point: 240-243° C.

13-(4-(Dimethylamino)phenyl)-9,10-dihydro-9,10-[3,4]epipyrroloanthracene-12,14-dione (40)

$^1$H-NMR (400 MHz, DMSO-d$_6$) δ (ppm): 7.50 (2H, q, J=3.2 Hz), 7.28 (2H, q, J=3.2 Hz), 7.18-7.21 (4H, m), 6.58 (2H, d, J=9.2 Hz, aniline p-substitution), 6.20 (2H, d, J=9.0 Hz, aniline p-substitution), 4.84 (2H, s), 3.35 (2H, s), 2.85 (6H, s, dimethyl). $^{13}$C-NMR (600 MHz, DMSO-d$_6$) δ (ppm): 176.74 (2C, C=O), 150.48 (C—N-dimethyl), 142.10 (2C), 139.72 (2C), 127.39 (2C), 126.92 (2C), 126.70 (2C), 125.14 (2C), 124.69 (2C, aniline p-substitution), 120.53, 112.23 (2C, aniline p-substitution), 46.06 (2C, aliphatic CH), 45.89 (2C, aliphatic CH), 40.19 (2C, dimethyl). ν$_{max}$/cm$^{-1}$: 3033, 2948 (C—H stretch), 1709 (C=O stretch), 1392 (dimethyl), 1246, 1186 (C—N stretch). m/z: 395.3 (58%, [M+H]$^+$; C$_{26}$H$_{22}$N$_2$O$_2$ predicted mass 394.47). Melting Point: 243-245° C.

13-(p-tolyl)-9,10-dihydro-9,10-[3,4]epipyrroloanthracene-12,14-dione (41)

$^1$H NMR (400 MHz, DMSO-d6) δ (ppm): 7.52-7.50 (2H, m), 7.31-7.28 (2H, m), 7.18-7.29 (4H, m), 7.12 (2H, d, J=8.52 Hz), 6.30 (2H, dt, J=1.72, J=1.84), 4.85 (2H, s), 3.38 (2H, t, J=0.56 Hz), 2.25 (3H, s); $^{13}$C NMR (400 MHz, DMSO-d6) δ (ppm) 176.61 (2C), 142.22 (2C), 139.86, 138.59, 129.84 (2C), 129.77 (2C), 127.17 (2C), 126.92 (2C), 126.84 (2C), 125.35 (2C), 124.93 (2C), 47.64 (2C), 45.79 (2C), 21.21.

13-(3-Methoxyphenyl)-9-nitro-9,10-dihydro-9,10-[3,4]epipyrroloanthracene-12,14-dione (42)

$^1$H-NMR (400 MHz, DMSO-d$_6$) δ (ppm): 7.51 (2H, q, J=8.6 Hz), 7.30 (2H, q, J=8.6 Hz), 7.19-7.24 (4H, m), 6.91 (1H, d, J=10.3 Hz), 6.08 (1H, s), 6.06 (1H, s), 5.80 (1H, s), 4.86 (2H, s), 3.65 (3H, s, methyl), 3.40 (2H, s). $^{13}$C-NMR (600 MHz, DMSO-d$_6$) δ (ppm): 176.17 (2C, C=O), 159.68 (aniline C—OMe), 141.92 (2C), 139.65 (2C), 130.00 (aniline), 126.95 (2C), 126.70 (2C), 124.93 (2C), 124.70 (2C), 124.48 (aniline), 119.21 (aniline), 114.53 (aniline), 112.62 (aniline), 55.96 (methyl), 46.03 (2C, aliphatic CH), 44.56 (2C, aliphatic CH). ν$_{max}$/cm$^{-1}$: 3011, 2948 (C—H stretch), 1712 (C=O stretch), 1247 (C—N stretch), 1200, 1166 (C—O stretch). m/z: 382.3 (36%, [M+H]$^+$; C$_{26}$H$_{16}$NO$_3$ predicted mass 381.43). Mp: 200-201° C.

13-(3-(Dimethylamino)phenyl)-9,10-dihydro-9,10-[3,4]epipyrroloanthracene-12,14-dione (43)

$^1$H-NMR (400 MHz, DMSO-d$_6$) δ (ppm): 7.49-7.52 (2H, m), 7.30-7.33 (2H, m), 7.18-7.23 (6H, m), 7.10 (1H, t, J=8.4 Hz), 6.64 (1H, d, J=10.4 Hz), 5.80 (1H, d, J=8.6 Hz), 5.40 (1H, s), 4.86 (2H, s), 2.78 (6H, s, dimethyl). $^{13}$C-NMR (600 MHz, DMSO-d$_6$) δ (ppm): 175.53 (2C, C=O), 150.22 (aniline C—N-dimethyl), 141.19 (2C), 139.25 (2C), 132.46 (aniline), 128.99 (aniline), 125.97 (4C), 124.11 (4C), 114.09 (aniline), 112.17 (aniline), 110.27 (aniline), 47.93 (2C, aliphatic CH), 46.59 (2C, aliphatic CH), 44.82 (2C, dimethyl). ν$_{max}$/cm$^{-1}$: 2967, 2948 (C—H stretch), 1709 (C=O stretch), 1246 (C—N stretch). Mp: 228-230° C.

3-(12,14-Dioxo-9,10-dihydro-9,10-[3,4]epipyrroloanthracen-13-yl)benzonitrile (44)

$^1$H-NMR (600 MHz, DMSO-d6) δ (ppm): 7.81-7.83 (1H, m, benzonitrile), 7.58 (2H, t, J=8.1 Hz, benzonitrile), 7.50-7.52 (1H, m, benzonitrile), 7.30-7.32 (4H, m), 7.18-7.22 (2H, m), 6.85-6.86 (1H, m), 6.76-6.77 (1H, m), 4.87 (2H, s), 3.45 (2H, s). $^{13}$C-NMR (600 MHz, DMSO-d6) δ (ppm): 175.53 (2C, C=O), 141.39 (2C, benzene C), 139.23 (2C, benzene C), 132.46 (aniline), 132.36 (aniline), 131.40 (aniline), 130.54 (aniline), 129.72 (aniline), 126.66 (2C), 126.39 (2C), 124.79 (2C), 124.40 (2C), 117.56 (aniline CEN), 111.86 (aniline C-cyano), 46.02 (2C, aliphatic C—H), 44.41 (2C, aliphatic C—H); ν$_{max}$/cm$^{-1}$: 3076, 2970 (C—H stretch), 2239 (CEN stretch), 1712 (C=O stretch), 1195 (C—N stretch). Mp: 262-264° C.

13-(m-Tolyl)-9,10-dihydro-9,10-[3,4]epipyrroloanthracene-12,14-dione (45)

$^1$H NMR (400 MHz, DMSO-d6) δ (ppm): 7.50-7.52 (2H, m), 7.30-7.32 (2H, m), 7.19-7.24 (5H, m), 7.43 (1H, d, J=8.02 Hz), 6.21 (1H, d, J=8.52), 6.17 (1H, s), 4.85 (2H, s), 3.39 (2H, t, J=0.64 Hz), 2.21 (3H, s); $^{13}$C NMR (400 MHz, DMSO-d6) δ (ppm) 176.60, 172.67, 142.20 (2C), 139.88 (2C), 138.91, 132.38, 129.68, 129.23, 127.67, 127.18 (2C), 126.94 (2C), 125.40 (2C), 124.94 (2C), 124.26 (2C), 47.75 (2C), 45.88 (2C), 21.24.

Heterocyclic Analogues (46-48)

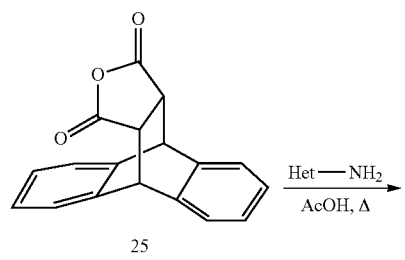

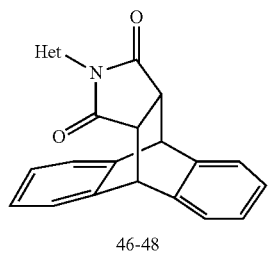

46-48

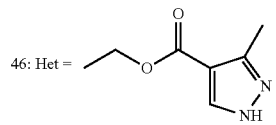

46: Het =

47: Het =

48: Het =

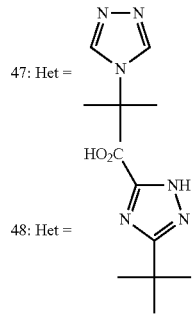

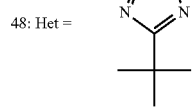

Ethyl 3-(12,14-dioxo-9,10-dihydro-9,10-[3,4]epipyrroloanthracen-13-yl)-pyrazole-4-carboxylate (46)

$^1$H-NMR (400 MHz, DMSO-d$_6$) δ (ppm): 7.46 (2H, q, J=3.2 Hz, pyrazole), 7.33 (4H, q, J=3.4 Hz), 7.18 (4H, qq, J=2.3 Hz, 3.2 Hz), 4.86 (2H, s), 4.57 (2H, s), 2.99 (2H, s), 1.90 (3H, s, methyl). $^{13}$C-NMR (600 MHz, DMSO-d$_6$) δ (ppm): 171.13 (2C, C=O), 166.71 (O=C—O), 149.97 (pyrazole), 140.64 (4C), 138.64 (pyrazole), 126.21 (2C), 126.17 (2C), 124.45 (2C), 124.05 (2C), 103.96 (pyrazole), 67.62 (aliphatic pyrazole CH$_2$), 47.82 (2C, aliphatic CH), 44.40 (2C, alphatic CH), 13.83 (methyl). ν$_{max}$/cm$^{-1}$: 2967, 2948 (C—H stretch), 1710 (C=O stretch), 1607 (N—H stretch), 1246 (C—N stretch), 1199, 1166 (C—O stretch). m/z: 412.1 (12%, [M−H]$^-$; C$_{24}$H$_{19}$N$_3$O$_4$ predicted mass 413.43). Mp: 243-244° C.

13-(1,2,4-triazol-4-yl)-9,10-dihydro-9,10-[3,4]epipyrroloanthracene-12,14-dione (47)

$^1$H-NMR (400 MHz, DMSO-d$_6$) δ (ppm): 7.71 (2H, s, triazole), 7.54 (1H, q, J=8.6 Hz), 7.48 (1H, q, J=8.6 Hz), 7.18-7.35 (6H, m), 4.94 (1H, s), 4.88 (1H, s), 3.66 (1H, s), 3.58 (1H, s). $^{13}$C-NMR (400 MHz, DMSO-d$_6$) δ (ppm): 172.22 (2C, C=O), 142.03 (2C, triazole), 141.32 (2C, benzene C), 139.50 (2C, benzene C), 127.69 (2C), 127.21 (2C), 125.50 (2C), 125.20 (2C), 48.51 (aliphatic CH), 45.62 (aliphatic CH), 45.20 (aliphatic CH), 44.82 (aliphatic CH). ν$_{max}$/cm$^{-1}$: 3082, 2974 (C—H stretch), 1749 (C=O stretch), 1463 (C=N stretch), 1296 (C—N stretch). Mp: 252-254° C.

3-(12,14-Dioxo-9,10-dihydro-9,10-[3,4]-epipyrrolanthracene-13-yl)-1H-1,2,4-tiazole-5-carboxylic acid (48)

Mp 248-252° C.; $^1$H NMR (600 MHz, CDCl$_3$) δ (ppm): 7.36-7.41 (2H, m), 7.29-7.32 (2H, m), 7.24 (1H, s), 7.17-7.20 (2H, m), 7.14-7.16 (1H, m), 4.88 (2H, t, J=1.56 Hz), 3.43 (2H, t, J=1.74); $^{13}$C NMR (600 MHz, CDCl$_3$) δ (ppm): 174.26, 170.43, 141.16, 140.61, 138.27, 138.07, 127.76, 127.40, 127.15, 126.94, 125.20, 125.07, 124.40, 124.35, 47.99, 47.95, 45.65, 45.42; ν$_{max}$/cm$^{-1}$: 1718 (C=O stretch), 1475 (C—H bend), 1188 (C—H bend).

Ester and Amide Derivatives (49-55)

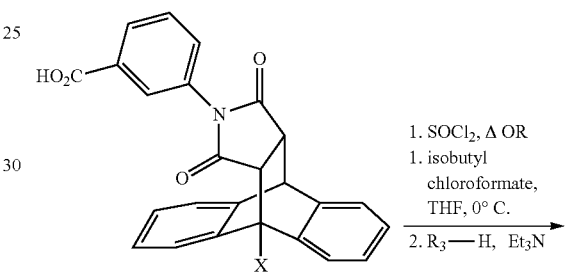

2: X = NO$_2$
26: X = H

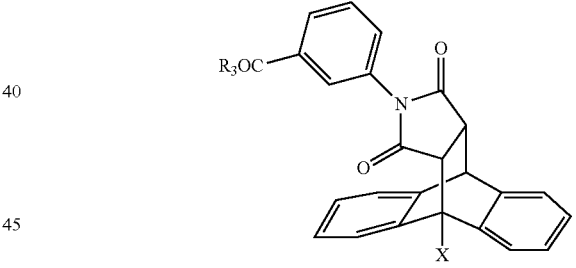

49: X = NO$_2$, R3—H = n-butanol
50: X = H, R3—H = 3-(N,N-dimethylamino)propanol
51: X = NO$_2$, R3—H = 5-hydroxypentan-2-one
52: X = NO$_2$, R3—H = benzylamine
53: X = NO$_2$, R3—H = 4-(aminomethyl)benzoic acid

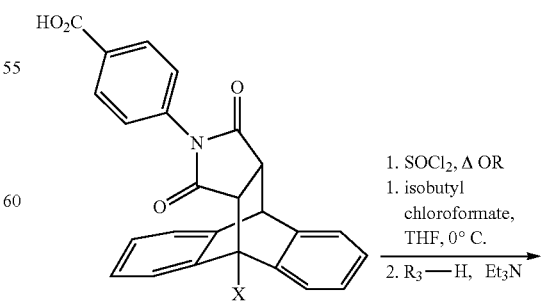

8: X = NO$_2$
32: X = H

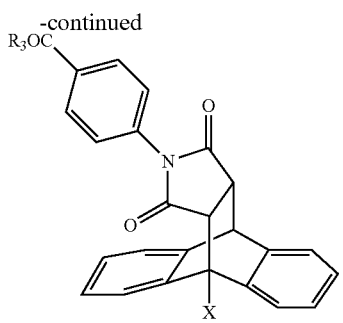

54: X = NO₂, R3—H = n-butanol
55: X = H, R3—H = 4-(aminomethyl)benzoic acid

Method: The benzoic acid derivative (2 mmol) and thionyl chloride (5 mL) were heated under reflux for 2 hours. Excess thionyl chloride was evaporated under a stream of nitrogen with a cold water trap. After cooling, triethylamine (1 molar equivalent) and an excess amount of alcohol or amine reagent (about 8-10 mL) were added and the mixture stirred at room temperature until complete by TLC. The mixture was poured into water to obtain the product as a precipitate, which was filtered and air-dried.

Alternate method: Isobutyl chloroformate (2.1 mmol) was added to the benzoic acid derivative (2 mmol) and trethylamine (2.1 mmol) in THF (10 mL), cooled to below 0° C. in an ice-salt bath, with stirring. The mixture was allowed to warm to room temperature over a period of 2 hours. After re-cooling to 0° C., the alcohol or amine reagent (2.0 mmol) in THF (10 mL) was added and the mixture stirred at room temperature until complete by TLC. The solvent was evaporated to give the crude product.

Butyl 3-((9-nitro-12, 14-dioxo-9,10-dihydro-9,10-[3,4]epipyrroloanthracen-13-yl) benzoate (49)

Mp: 263-265° C.; $^1$H NMR (600 MHz, DMSO-d$_6$): δ 7.90 (1H, d, J=7.9 Hz), 7.70 (H, d, J=7.2 Hz), 7.62 (1H, m, Ar—H), 7.46-7.52 (2H, m, Ar—H), 7.34-7.43 (4H, m), 7.01-7.05 (2H, m, Ar—H), 6.75 (1H, dd, J=7.6, 1.9 Hz, Ar—H), 5.07 (1H, d, J=2.9 Hz, CH), 4.47 (1H, dd, J=7.4, 1.4 Hz, CH), 4.26 (2H, t, J=6.7 Hz, CH$_2$), 3.68 (1H, m, CH), 1.68 (2H, quintet, J=7.6 Hz, CH$_2$), 1.39 (2H, sextet, J=7.5 Hz, CH$_2$), 0.93 (3H, t, J=7.6 Hz, CH$_3$); $^{13}$C NMR (d6-DMSO): δ 174.2, 173.0, 164.6, 140.0, 138.5, 133.5, 131.1, 129.7, 127.4, 127.1, 124.8, 123.2, 120.1, 93.2, 64.7, 49.5, 47.5, 44.5, 30.1, 18.7, 13.5; v$_{max}$/cm$^{-1}$: 3392 (OH str), 2956 (CH str), 1708 (C=O), 1450 (Ar—C=C str), 1389 (Ar—C=C str).

3-(Dimethylamino) propyl 3-(12, 14-dioxo-9,10-dihydro-9,10-[3,4]epipyrrolo-anthracen-13-yl) benzoate (50)

Mp: 96-101° C.; $^1$H NMR (DMSO-d6): δ, 7.88 (1H, d, J=7.9 Hz) 7.48-7.51 (3H, m, Ar—H), 7.30 (2H, m, Ar—H), 7.17-7.22 (4H, m, Ar—H), 6.98 (1H, d, J=1.4 Hz), 6.76 (1H, d, J=7.9 Hz), 4.86 (1H, m), 4.27 (1H, t, J=6.5 Hz), 2.27 (2H, t, J=7.7 Hz, NCH$_2$), 2.11-2.14 (6H, s, N(CH$_3$)$_2$), 1.53 (2H, quin, J=6.5 Hz, CH$_2$); $^{13}$C NMR (DMSO-d6): δ 175.8, 164.7, 141.5, 139.3, 132.2, 131.3, 130.7, 129.5, 129.2, 127.3, 126.7, 126.4, 124.8, 124.4, 63.5, 59.3, 56.3, 55.5, 46.0, 44.5, 30.1, 26.3; v$_{max}$/cm$^{-1}$: 3396 (OH str), 2863 (Ar—CH), 2781 (Ar—CH), 1701 (C=O), 1489 (Ar—C=C), 1448 (Ar—C=C).

4-Oxopentyl-3-(9-nitro-12,14-dioxo-9,10-dihydro-9,10-[3,4]-epipyrrolanthracene-13-yl)benzoate (51)

$^1$H NMR (600 MHz, CDCl$_3$) δ (ppm): 7.43 (2H, m), 7.19-7.20 (1H, m), 7.06-7.07 (1H, m), 6.93 (1H, m), 6.85-6.86 (4H, m), 6.73 (1H, d, J=1.50 Hz), 6.64 (1H, s), 6.56-6.57 (1H, m), 4.42-4.44 (2H, m), 4.06 (1H, d, 8.94 Hz), 4.00-4.01 (2H, m), 3.81 (1H, d, J=5.70 Hz), 3.61 (2H, q, J=6.54 Hz), 3.08-3.14 (1H, m), 2.75 (2H, d, J=6.54 Hz), 2.06 (1H, t, J=1.86 Hz); $^{13}$C NMR (600 MHz, CDCL3) δ (ppm): 172.93, 172.87, 171.68, 166.72, 137.86, 137.73, 135.90, 135.80, 135.47, 132.69, 131.45, 128.57, 127.64, 127.35, 126.40, 126.34, 126.13, 125.82, 124.17, 123.33, 123.28, 122.54, 92.10, 48.16, 46.68, 44.51, 26.82, 24.34, 17.96, 17.61.

N-Benzyl-3-(9-nitro-12,14-dioxo-9,10-dihydro-9,10-[3,4]epipyrroloanthracen-13-yl)benzamide (52)

$^1$H NMR (600 MHz, CDCl$_3$) δ (ppm): 7.46 (1H, d, J=6.54 Hz), 7.22-7.34 (8H, m), 7.17 (2H, m), 7.09 (1H, t, J=5.34 Hz), 6.82 (1H, t, J=1.92 Hz), 6.58 (1H, dd, J=1.38 Hz, J=0.84 Hz), 4.38-4.42 (1H, m), 3.65 (1H, q, J=7.02 Hz), 3.01 (3H, q, J=7.38); $^{13}$C NMR (600 MHz, DMSO-d6) δ (ppm): 173.97, 172.54, 169.99, 138.65, 138.25, 137.99, 136.94, 136.21, 135.53, 133.83, 131.06, 129.35, 129.16, 128.78, 128.70, 128.59, 128.42, 127.96, 127.87, 127.74, 127.65, 127.38, 125.24, 124.96, 124.14, 123.98, 120.99, 93.16, 48.91, 45.92, 45.65, 43.60.

4-(3-(9-Nitro-12,14-dioxo-9,10-dihydro-9,10-[3,4]epipyrroloanthracen-13-yl)benzamido)methyl)benzoic acid (53)

$^1$H NMR (600 MHz, CDCl$_3$) δ (ppm): 8.19 (1H, t, J=5.82), 7.04-7.07 (2H, m), 6.78-6.82 (1H, m), 6.76-6.77 (1H, m), 6.65-6.67 (1H, m), 6.59-6.60 (1H, m), 6.51-6.53 (6H, m), 6.37 (1H, s), 6.34 (1H, s), 6.28 (1H, s), 6.19-6.27 (1H, t, J=7.56 Hz), 4.12-4.13 (2H, m), 3.27 (1H, d, J=6.66 Hz), 2.78-2.79 (1H, m), 2.34 (2H, d, J=6.54 Hz); $^{13}$C NMR (600 MHz, CDCl3) δ (ppm): 172.43, 172.34, 171.26, 165.79, 137.51, 137.41, 135.38, 135.21, 132.16, 129.77 (2C), 128.79, 127.96, 127.83, 127.30, 126.99, 126.69, 126.01, 125.69 (2C), 125.50, 125.20, 123.62, 122.90, 121.82, 118.75, 91.52, 47.42, 45.99, 43.63;

Butyl 4-((9-nitro-12, 14-dioxo-9,10-dihydro-9,10-[3,4]epipyrroloanthracen-13-yl) benzoate (54)

Mp: 258-272° C.; $^1$H NMR (d6-DMSO): δ 7.87 (2H, d, J=8.0 Hz Ar—H); 7.69 (1H, m, Ar—H), 7.61 (1H, m, Ar—H), 7.35-7.45 (5H, m, Ar—H), 7.04 (1H, d, J=7.7 Hz, Ar—H), 6.58 (2H, d, J=8.0 Hz, Ar—H), 5.06 (1H, d, J=2.6 Hz, CH), 4.48 (1H, m, CH), 4.25 (2H, t, J=6.5 Hz), 3.67 (1H, m, CH), 1.65 (2H, quintet, J=7.8 Hz, CH$_2$), 1.39 (2H, sextet, J=7.5 Hz, CH$_2$), 0.90 (3H, t, J=7.4 Hz, CH$_3$)$^{13}$C NMR (d6-DMSO): δ 174.1, 172.9, 129.8, 128.4, 127.4, 126.2, 125.3, 124.8, 123.2, 120.1, 93.2, 49.0, 47.5, 45.0, 44.5, 30.1, 18.6, 13.5; v$_{max}$/cm$^{-1}$: 3365 (OH str), 2917 (CH str), 1708 (C=O), 1458 (Ar—C=C str).

4-((4-(12,14-dioxo-9,10-dihydro-9,10-[3,4]epipyrroloanthracen-13-yl)benzamido)methyl)benzoic acid (55)

Mp: 251-256° C.; $^1$H NMR (DMSO-d6): δ 0.83-0.85 (1H, m, CH), 0.93-0.95 (2H, t, CH$_2$ J=7.02 Hz), 1.22-1.26 (3H, m, CH$_2$) 1.89 (2H s, CH), 2.07 (1H, s, CH), 3.85 (1H, s, CH), 4.86 (1H, m, CH), 6.55 (1H, m, Ar—H), 7.18-7.20 (3H, m, Ar—H), 7.30-7.31 (3H, m, Ar—H), 7.51 (2H, m, Ar—H), 7.87 (2H, m, Ar—H); v$_{max}$/cm$^{-1}$: 3019 (OH str), 2848 (Ar—CH), 2622 (Ar—CH), 1703 (C=O), 1489 (Ar—C=C), 1455 (Ar—C=C).

Protein Binding Results

ELISA assay of S100P-RAGE binding was carried out using the method of Padilla et al. (Padilla, L., Dakhel, S., & Hernandez, J. (2014). S100 to receptor for advanced glycation end-products binding assay: Looking for inhibitors. Biochemical and Biophysical Research Communications, 446(1), 404-409. doi:10.1016/j.bbrc.2014.02.143). FIGS. 6A to 6H illustrate the effect of drugs on the binding between 1 μM S100P and 30 nM RAGE in ELISA assay wherein n=3 from one plate.

Figure 6A:
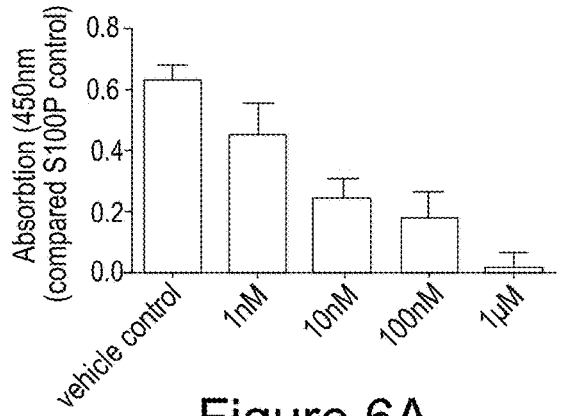
FIGS. 6A to 6H illustrate the effect of drugs on the binding between 1 μM S100P and 30 nM RAGE in ELISA assay wherein n=3 from one plate.

FIG. 6A illustrates the results for 13-phenyl-9,10-dihydro-9,10-[3,4]epipyrroloanthracene-12,14-dione (31).

Figure 6B:
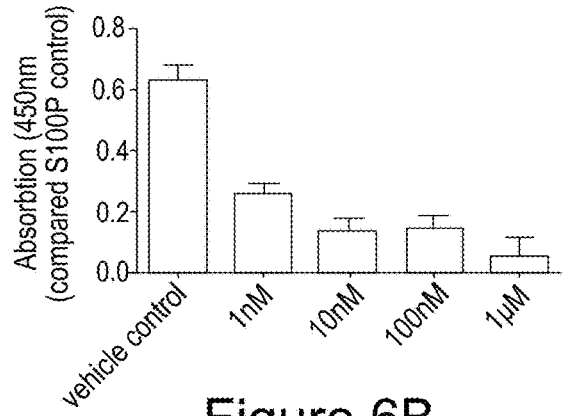

FIG. 6B illustrates the results for 13-(3-fluorophenyl)-9,10-dihydro-9,10-[3,4]epipyrroloanthracene-12,14-dione (28)

Figure 6C:
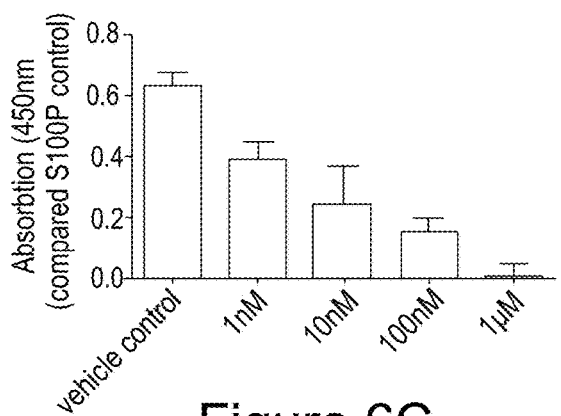

FIG. 6C illustrates the results for 13-(3-fluorophenyl)-9-nitro-9,10-dihydro-9,10-[3,4]epipyrroloanthracene-12,14-dione (5)

Figure 6D:
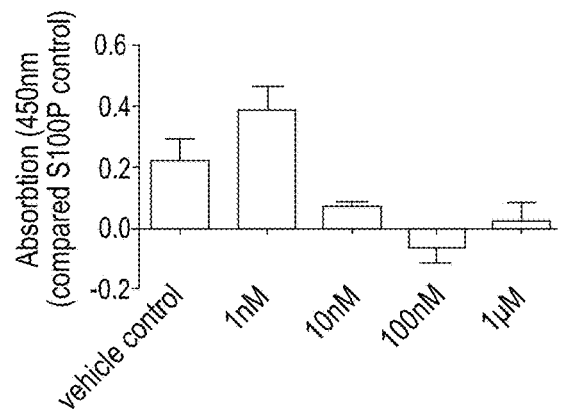

FIG. 6D illustrates the results for 13-(4-fluorophenyl)-9,10-dihydro-9,10-[3,4]epipyrroloanthracene-12,14-dione (34)

Figure 6E:
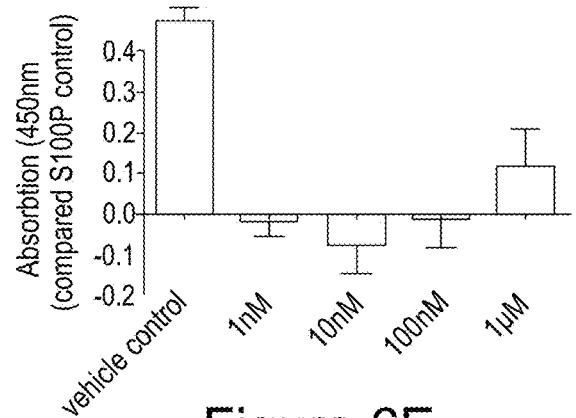

FIG. 6E illustrates the results for 13-(4-chlorophenyl)-9,10-dihydro-9,10-[3,4]epipyrroloanthracene-12,14-dione (35)

Figure 6F:
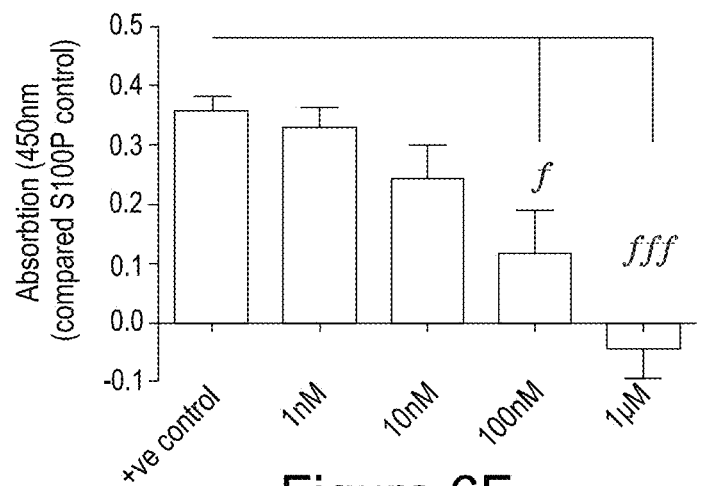

FIG. 6F illustrates the results for 3-(9-nitro-12,14-dioxo-9,10-dihydro-9,10-[3,4]epipyrroloanthracen-13-yl)benzoic acid (2)

Figure 6G:
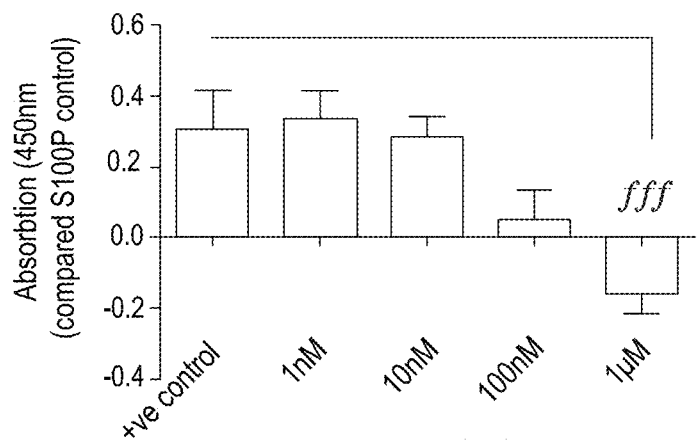
Figure 6H:
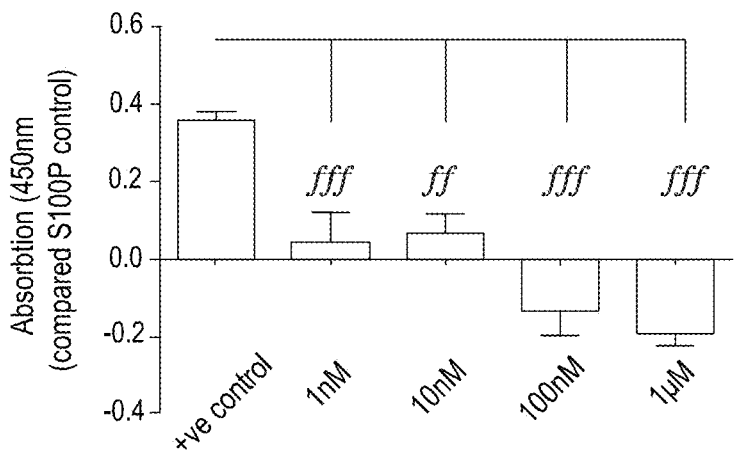

FIG. 6G illustrates the results for Ethyl 3-(9-nitro-12,14-dioxo-9,10-dihydro-9,10-[3,4]epipyrroloanthracen-13-yl)benzoate (3)+RAGE FIG. 6H illustrates the results for 4-(9-nitro-12,14-dioxo-9,10-dihydro-9,10-[3,4]epipyrroloanthracen-13-yl)benzoic acid (8)

The invention claimed is:

1. A compound of the general formula (A)

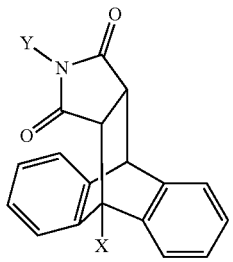

(A)

or a pharmaceutically acceptable salt, solvate, hydrate, polymorph, prodrug, codrug, cocrystal, tautomer, racemate, stereoisomer or mixture thereof, wherein:

X is independently $NO_2$ or H; and
Y is

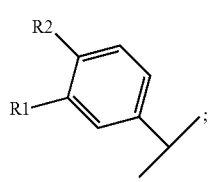

(B)

wherein R2 is hydrogen or a substituent selected from a carboxy, ester, fluorine, iodine, alkyl, aldehyde, amino, cyano, and ketone, and wherein the alkyl is not methyl and is not acetylaldehyde; and wherein R1 is hydrogen or a substituent selected from a carboxy, ester, fluorine, iodine, alkyl, aldehyde, amino, cyano, and ketone;

wherein when R1 is hydrogen then R2 is the substituent selected from a carboxy, ester, fluorine, iodine, alkyl, aldehyde, amino, cyano, and ketone, and wherein the alkyl is not methyl and is not acetylaldehyde; and wherein when R2 is hydrogen then R1 is the substituent selected from a carboxy, ester, fluorine, iodine, alkyl, aldehyde, amino, cyano, and ketone.

2. A compound according to claim 1 wherein Y has the general formula (B):

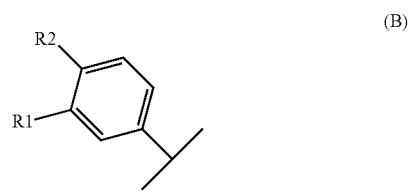

(B)

wherein R1 and R2 are independently selected from the following combinations:

|       | R1        | R2        |
|-------|-----------|-----------|
| i     | $CO_2H$   | H         |
| ii    | $CO_2Et$  | H         |
| iii   | F         | H         |
| iv    | Cl        | H         |
| v     | F         | H         |
| vi    | $NO_2$    | H         |
| vii   | I         | H         |
| viii  | tBu       | H         |
| ix    | methyl    | H         |
| x     | $OCH_3$   | H         |
| xi    | $N CH_3 CH_3$ | H     |
| xii   | CN        | H         |
| xiii  | H         | $CO_2H$   |
| xiv   | H         | $CO_2Et$  |
| xv    | H         | F         |
| xvi   | H         | Cl        |
| xvii  | H         | F         |
| xviii | H         | $NO_2$    |
| xix   | H         | I         |
| xx    | H         | tBu       |
| xxi   | H         | methyl    |
| xxii  | H         | $OCH_3$   |
| xxiii | H         | $N CH_3 CH_3$ |
| xxiv  | H         | CN        |
| xxv   | H         | H         |
| xxvi  | CO—R3     | H         |
| xxvii | H         | CO—R3     | wherein R3 is selected from:

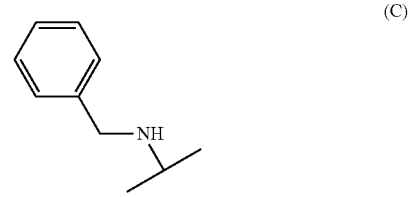

(C)

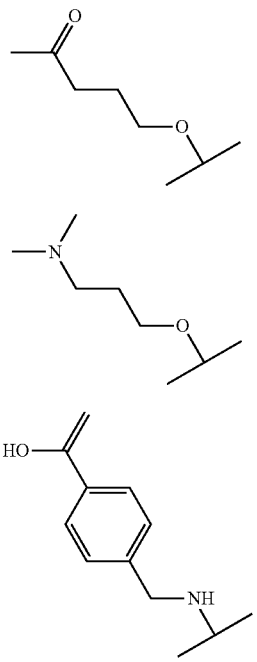

(D)

(E)

(F)

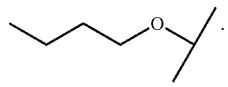

(G)

3. A compound according to claim 2 wherein X is $NO_2$, R1 is —$CO_2H$ and R2 is H.

4. A compound according to claim 2 wherein X is $NO_2$, R1 is —$CO_2Et$ and R2 is H.

5. A compound according to claim 2 wherein X is $NO_2$, R1 is H and R2 is —$CO_2H$.

6. A compound according to claim 2 wherein X is H, R1 is —$CO_2H$ and R2 is H.

7. A compound according to claim 2 wherein X is H, R1 is F and R2 is H.

8. A compound according to claim 2 wherein X is H, R1 is H and R2 is F.

9. A pharmaceutical composition comprising one or more compounds as claimed in claim 1 and pharmaceutically acceptable excipients, adjuvants, diluents and/or carriers.

* * * * *